US007989185B2

(12) United States Patent
Pourmand et al.

(10) Patent No.: US 7,989,185 B2
(45) Date of Patent: Aug. 2, 2011

(54) RAPID, INFORMATIVE DIAGNOSTIC ASSAY FOR INFLUENZA VIRUSES INCLUDING H5N1

(75) Inventors: Nader Pourmand, San Mateo, CA (US); Lisa Diamond, Ross, CA (US); Jochen Kumm, Redwood City, CA (US); Ronald W. Davis, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 667 days.

(21) Appl. No.: 11/945,960

(22) Filed: Nov. 27, 2007

(65) Prior Publication Data

US 2009/0123909 A1 May 14, 2009

Related U.S. Application Data

(60) Provisional application No. 60/861,603, filed on Nov. 29, 2006.

(51) Int. Cl.
*C12Q 1/68* (2006.01)
*C12P 19/34* (2006.01)

(52) U.S. Cl. .......................... 435/91.2; 435/6; 435/91.1

(58) Field of Classification Search ........................ None
See application file for complete search history.

(56) References Cited

U.S. PATENT DOCUMENTS

| | | | |
|---|---|---|---|
| 4,971,903 A | 11/1990 | Hyman |
| 6,015,664 A | 1/2000 | Henrickson et al. |
| 6,210,891 B1 | 4/2001 | Nyren et al. |
| 6,258,568 B1 | 7/2001 | Nyren |
| 6,274,320 B1 | 8/2001 | Rothberg et al. |
| 6,841,128 B2 | 1/2005 | Kambara et al. |
| 7,141,370 B2 | 11/2006 | Hassibi et al. |
| 2003/0082583 A1 | 5/2003 | Hassibi et al. |

OTHER PUBLICATIONS

Subbarao et al., "Characterization of an Avian Influenza A (H5N1) Virus Isolates from a Child with a Fetal Respiratory Illness," Science, Jan. 1998, vol. 279, pp. 393-396.*

Yuen et al., "Clinical features and rapid viral diagnosis of human disease associated with avian influenza A H5N1 virus." The Lancet, Feb. 1998, vol. 351, pp. 467-471.*

Gharizadeh et al., "Methodological improvements of pyrosequencing technology," Journal of Biotechnology, 2006, vol. 124, pp. 504-511.*

Jipling Li, et al., "Typing and Subtyping Influenza Virus Using DNA Microarrays and Multiplex Reverse Transcriptase PCR," Journal of Clinical Microbiology, Feb. 2001, vol. 39, No. 2, 696-704.

Ya Ha, et al., "H5 avian and H9 swine influenza virus hemagglutinin structures: possible origin of influenza subtypes," EMBO Journal, 2002, vol. 21, No. 5, 865-875.

Erich Hoffmann, et al., "Role of specific hemagglutinin amino acids in the immunogenicity and protection of H5N1 influenza virus vaccines," PNAS, Sep. 6, 2005, vol. 102, No. 36, 12915-12920.

Baback Gharizadeh, et al., "Methodological improvements of pyrosequencing technology," Journal of Biotechnology, 2006, 4207, 1-8.

* cited by examiner

*Primary Examiner* — Young J Kim

(74) *Attorney, Agent, or Firm* — David J. Aston; Peters Verny, LLP

(57) ABSTRACT

A rapid diagnostic assay for influenza virus, particularly avian influenza and more particularly H5N1, is described. The assay is based on amplification of a significant portion of the hemagglutinin (HA) gene and sequencing of several loci within the HA gene, using techniques which can obtain real time sequence information from multiple sites of a target DNA, in particular pyrosequencing and bioluminescence regenerative cycle. The assay contemplates the use of information-rich subsequences within the HA gene, e.g., (1) a glycosylation sequon; (2) receptor binding site; and (3) HA1/HA2 cleavage site. Other subsequences for sequencing include strain and clade markers, which vary among H5N1 strains.

12 Claims, 14 Drawing Sheets

800 bp →

3A Primer F-H5N1-site1SM-seq:
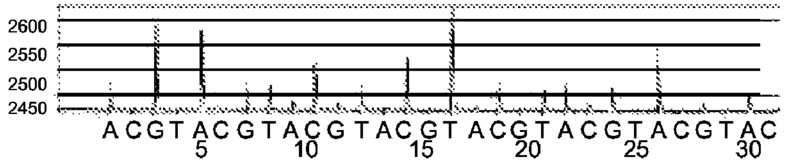
Obtained sequence: 5' -
AGGGAAAGTCCTCCTTTTTCAGAAA
3B Primer F-H5N1-site2AS-seq:
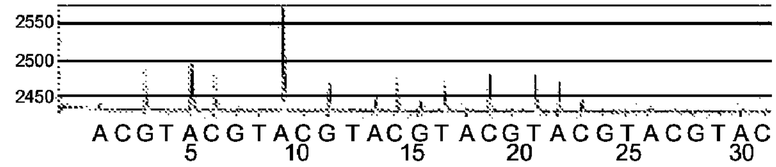
Obtained sequence: 5' -
GTACATACCCAACAATA
3C Primer F-H5N1-site3SM-seq:
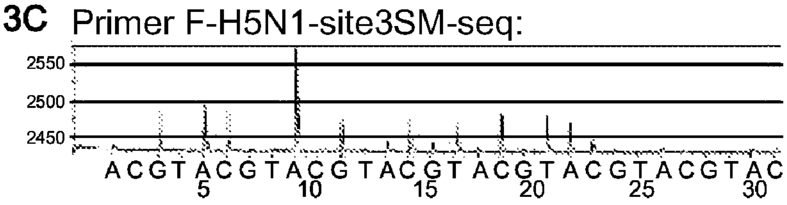
Obtained sequence: 5' – GACAAAGCTCTA-3'
3D Primer R-H5N1-site4AS-seq:
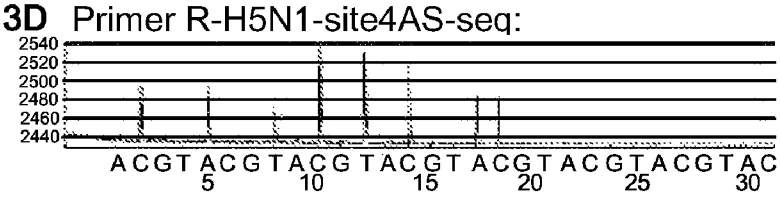
Obtained sequence: 3' – GTAGGAAGGTG-5'
Fig. 3A-D

3E Primer F-H5N1-site5SM-seq:
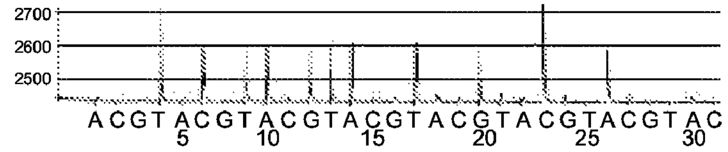
Obtained sequence: 5' –TTCTAGTATGCCA-3'
3F Primer R-H5N1-site6AS-seq:
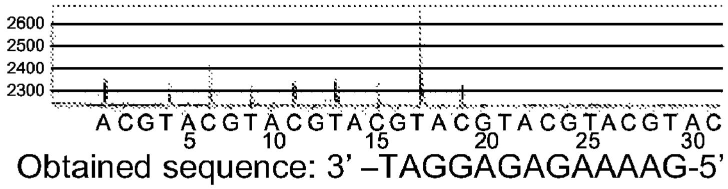
Obtained sequence: 3' –TAGGAGAGAAAAG-5'
3G Primer R-H5N1-CM1:
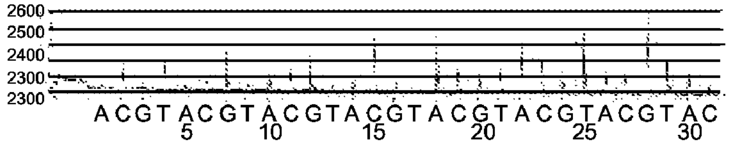
Obtained sequence: 3' –GACCTGC-5'
3H Primer F-H5N1-CM2:
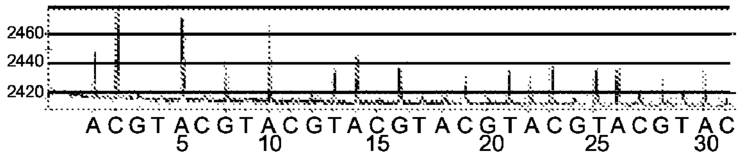
Obtained sequence: 5' –ACCAAGAATAG-3'
3I Primer R-H5N1-CM2:
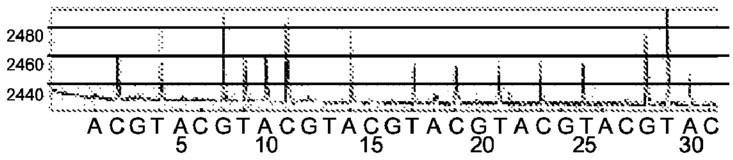
Obtained sequence: 3' –
GAACCATGGTTAGAGA-5'
Fig. 3E-I

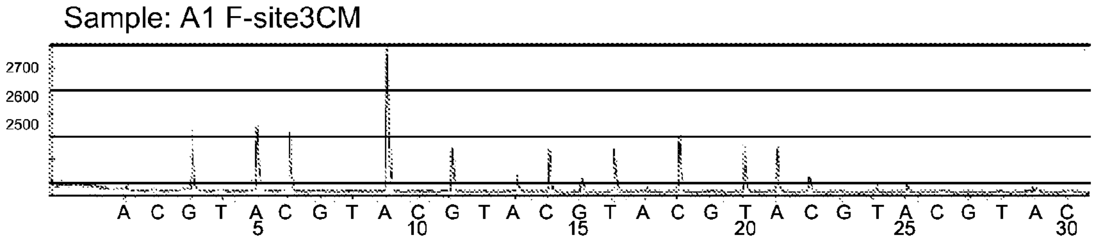
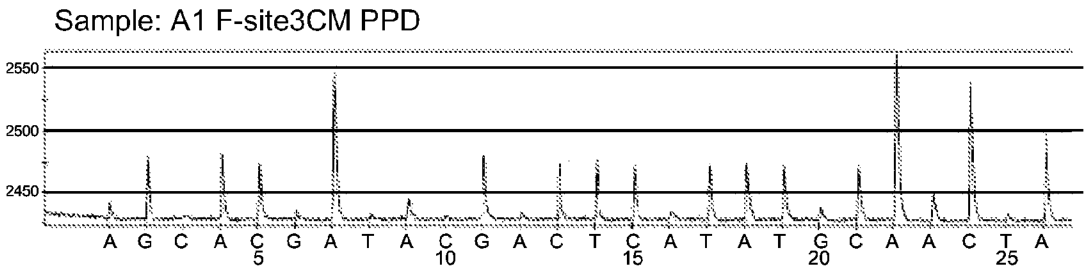
Fig. 4

```
CLUSTAL W (1.83) multiple sequence alignment

VN120304          TCAATGACTATGAAGAATTGAAACA.CCTATTGAGCAGAATAAACCATTTTGAGAAAATTC
1.VNHN3040805     TCAATGACTATGAAGAATTGAAACA.CTTATTGAGCAGAATAAACCATTTTGAGAAAATTC
VNJP1405          TCAATGACTATGAAGAATTGAAACA.CCTATTGAGCAGAATAAACCATTTTGAGAAAATTC
HK21303           TCAACGACTATGAAGAATTGAAACA.CCTATTGAGCAGAATAAACCATTTTGAGAAAATTC
CkKoreaES03       TCAACGACTATGAAGAACTGAAACA.CCTATTGAGCAGAATAAACCATTTTGAAAAAATTC
Indonesia505      TCAACGACTATGAAGAACTGAAACA.CCTATTGAGCAGAATAAACCATTTTGAGAAAATTC
GsGuangdong196    TCAACGACTATGAAGAACTGAAACA.CCTATTGAGCAGAACAAACCATTTTGAGAAGATTC
HK15697           TCAACGACTATGAAGAACTGAAACA.CCTATTGAGCAGAATAAACCATTTTGAGAAAATCC
HK48397           TCAACGACTATGAAGAACTGAAACA.CCTATTGAGCAGAATAAACCATTTTGAGAAAATTC
                  **** ************ ******** ************ ************ ** ** *

VN120304          AGATCATCCCCAAAAGTTCTTGGTCC.ag.TCATGAAGCCTCATTAGG.GGTGAGCTCAGCAT
2.VNHN3040805     AGATCATCCCCAAAAGTTCTTGGCYC.ag.TCATGAAGCCTCATTAGG.GGTGAGCTCAGCAT
VNJP1405          AGATCATCCCCAAAAGTTCTTGGTCC.ag.TCATGAAGCCTCATTGGG.GGTGAGCGCAGCAT
HK21303           AGATCATCCCCAAAAATTCTTGGTCC.ag.TCATGAAGCCTCATTAGG.GGTGAGCTCAGCAT
CkKoreaES03       AGATCATCCCCAAAAGTTCTTGGTCC.ga.TCATGAAGCCTCATCAGG.GGTGAGCTCAGCAT
Indonesia505      AAATCATCCCCAAAAGTTCTTGGTCC.ga.TCATGAAGCCTCATCAGG.AGTGAGCTCAGCAT
GsGuangdong196    AGATCATCCCCCCAAGTTCTTGGTCC.aa.TCATGATGCCTCATCAGG.GGTGAGCTCAGCAT
HK15697           AGATCATCCCCAAAAGTTCTTGGTCC.aa.TCATGATGCCTCATCAGG.GGTGAGCTCAGCAT
HK48397           AGATCATCCCCAAAAGTTCTTGGTCC.aa.TCATGATGCCTCATCAGG.G.GTAAGCTCAGCAT
                  * *********  ** *******  *  ****** *******  ** ** *** ******

VN120304          GTCCATACC.AGGGAAAGTCCTCCTTTTTCAGA.AATGTGGT.ATGGCTTATCAAAAAGAACA
3.VNHN3040805     GTCCATACC.AGGGAAAGTCCTCCTTTTTCAGA.AATGTGGT.ATGGCTTATCAAAAAGAACA
VNJP1405          GTCCATACC.AGGGAAAGTCCTCCTTTTTCAGA.AATGTGGT.ATGGCTTATCAAAAAGAACA
HK21303           GTCCATACC.AAGGAAAGTCCTCCTTTTTCAGG.AATGTGGT.ATGGCTTATCAAAAAGAACA
CkKoreaES03       GTCCATACC.AGGGAAGGTCCTCCTTCTTCAGA.AATGTGGT.ATGGCTTATCAAAAAGAACA
Indonesia505      GTCCATACC.TGGGAAGTCCCTCCTTTTTTAGA.AATGTGGTATGGCTTATCAAAAAGAACA
GsGuangdong196    GTCCATACC.ATGGGAGGTCCTCCTTTTTCAGA.AATGTGGT.ATGGCTTATCAAAAAGAACA
HK15697           GTCCATACC.TTGGGAGGTCCTCCTTTTTCAGA.AATGTGGT.ATGGCTTATCAAAAAGAACA
HK48397           GTCCATACC.TTGGGAAGTCCTCCTTTTTCAGA.AATGTGGT.ATGGCTTATCAAAAAGAACA
                  *********  ** *   ******* ** ** *****************************

VN120304          GTACA.TACCCAACAATAAAGAGGAGCTACAATAATACCAACCAAGAAGATCTTTTGGTAC
4.VNHN3040805     GTACA.TACCCAACAATAAAGAGGAGCTACAATAACACCAACCAAGAAGATCTGTTGGTAC
VNJP1405          GTACA.TACCCAACAATAAAGAGGAGCTACAATAATACCAACCAAGAAGATCTTTTGGTAA
HK21303           ATGCA.TACCCAACAATAAAGAGGAGCTACAATAATACCAACCAAGAAGATCTTTTGGTAT
CkKoreaES03       GTGCA.TACCCAACAATAAAGAGAAGCTACAATAATACCAACCAAGAAGATCTTTTGGTAC
Indonesia505      GTACA.TACCCAACAATAAAGAAAAGCTACAATAATACCAACCAAGAAGATCTTTTGGTAC
GsGuangdong196    GTGCA.TACCCAACAATAAAGAGGAGCTACAATAATACCAACCAAGAAGATCTTTTAGTAC
HK15697           GTGCA.TACCCAACAATAAAGAGGAGCTACAATAATACCAACCAAGAAGATCTTTTGGTAC
HK48397           GTACA.TACCCAACAATAAAGAGGAGCTACAATAATACCAACCAAGAAGATCTTTTGGTAC
                  * ******************  *********** ***************** ** ***
```

Fig. 5A

```
VN120304          TGTGGGGGATTCACCA.TCCTAATGATGCGGCAGAGCA.GACAAAGCTCTATCAAAACC.CAA
5.VNHN3040805     TGTGGGGGATTCACCA.TCCTAATGATGCGGCAGAGCA.GACAAAGCTCTATCAAAAC.CAA
VNJP1405          TGTGGGGGATCCACCA.TCCTAATGATGCGGCAGAGCA.GACAAAGCTCTATCAAAACC.CAA
HK21303           TGTGGGGGATTCACCA.TCCTAATGATGCGGCAGAGCA.GACTAGGCTCTATCAAAACC.CAA
CkKoreaES03       TGTGGGGGATTCACCA.TCCAAATGATGCGGCAGAGCA.GACAAGACTCTATCAAAACC.CAA
Indonesia505      TGTGGGGAATTCACCA.TCCTAATGATGCGGCAGAGCA.GACAAGGCTATATCAAAACC.CAA
GsGuangdong196    TGTGGGGGATTCACCA.TCCTAATGATGCGGCAGAGCA.GACAAAGCTATATCAAAACC.CAA
HK15697           TGTGGGGGATTCACCA.TCCTAATGATGCGGCAGAGCA.GACAAAGCTCTATCAAAATC.CAA
HK48397           TGTGGGGGATTCACCA.TCCTAATGATGCGGCAGAGCA.GACAAAGCTCTATCAAAACCC.AA
                  ******* ** ********* ******************** *  ** ******** ****

VN120304          CCACCTATATTTCCGTTGGGA.CATCAACACTAAACCAGAGATTGGT.ACCA.ag.AATAGCTA
6.VNHN3040805     CCACCTATATTTCCGTTGGGA.CATCAACACTAAACCAGAGATTGGT.ACCA.ag.AATAGCTA
VNJP1405          CCACCTATATTTCCGTTGGGA.CATCAACACTAAACCAGAGATTGGT.ACCA.ag.AATAGCTA
HK21303           CCACCTACATTTCCGTTGGGA.CATCAACACTAAACCAGAGATTGGT.ACCA.aa.AATAGCTA
CkKoreaES03       CCACCTATATTTCCGTTGGGA.CATCAACACTAAACCAGAGATTGGT.ACCA.aa.AATAGCTA
Indonesia505      CCACCTATATTTCCATTGGGA.CATCAACACTAAACCAGAGATTGGT.ACCA.aa.AATAGCTA
GsGuangdong196    CCACTTACATTTCCGTTGGAA.CATCAACACTGAACCAGAGATTGGT.TCCA.ga.AATAGCTA
HK15697           CCACCTACATTTCCGTTGGAA.CATCAACACTGAACCAGAGATTGGT.TCCA.ga.AATAGCTA
HK48397           CCACCTACATTTCCGTTGGAA.CATCAACACTGAACCAGAGATTGGT.TCCA.ga.AATAGCTA
                  **** ** ****** **** *********** ************** ***  ********

VN120304          CTAGATCCAAAGTAAA.CGGG.CAAAGTGGA.AGGATG.GAGTTCTTCTGGACAATTTT.AAAGC
7.VNHN3040805     CTAGATCCAAAGTAAA.CGGG.CAAAGTGGA.AGGATG.GAGTTCTTCTGGACAATTTT.AAAAC
VNJP1405          CTAGATCCAAAGTAAA.CGGG.CAAAGTGGG.AGGATG.GAGTTCTTCTGGACAATTTT.AAAAC
HK21303           CTAGATCCAAAGTAAA.CGGG.CAAAATGGA.AGGATG.GAGTTCTTCTGGACAATTTT.AAAAC
CkKoreaES03       CTAGATCCAAAGTAAA.CGGG.CAAAGTGGA.AGGATG.GAGTTCTTCTGGACAATTTT.AAAAC
Indonesia505      CTAGATCCAAAGTAAACGGG.CAAAGTGGA.AGGATG.GAGTTCTTCTGGACAATTTT.AAAAC
GsGuangdong196    CTAGACCCAAAGTAAA.CGGG.CAAAGTGGA.AGAATG.GAGTTCTTCTGGACAATTTT.AAAGC
HK15697           CTAGACCCAAAGTAAA.CGGG.CAAAGTGGA.AGAATG.GAGTTCTTCTGGACAATTTT.AAAGC
HK48397           CTAGACCCAAAGTAAA.CGGG.CAAAGTGGA.AGAATA.GAGTTCTTCTGGACAATTTT.AAAGC
                  ***** ******************* *** ** ** ********************** *

VN120304          CGAATGATGCAATCAACTTCGAGAGTAATGGAAATTTCATTGCTCCAGAATATGCATACA
8.VNHN3040805     CGAATGATGCAATCAATTTCGAGAGTAATGGAAATTTCATTGCCCCAGAATATGCATACA
VNJP1405          CGAATGATGCAATCAACTTCGAGAGTAATGGAAATTTCATTGCTCCAGAATATGCATACA
HK21303           CGAATGATGCAATCAACTTCGAGAGCAATGGAAATTTCATTGCTCCAGAATATGCATACA
CkKoreaES03       CGAATGATGCAATCAGCTTTGAGAGTAATGGAAATTTCATTGCTCCAGAATATGCATACA
Indonesia505      CTAATGATGCAATCAACTTCGAGAGTAATGGAAATTTCATTGCTCCAGAATATGCATACA
GsGuangdong196    CGAATGATGCCATCAATTTCGAGAGTAATGGAAATTTCATTGCTCCAGAATATGCATACA
HK15697           CGAATGATGCCATCAATTTCGAGAGTAATGGAAATTTCATTGCTCCAGAATATGCATACA
HK48397           CGAATGATGCCATCAATTTCGAGAGTAATGGAAATTTCATTGCTCCAGAATATGCATACA
                  * ********* ****  ** ****** ***************** ****************

VN120304          AAATTGTCAAGAAAGGGGACTCAACAATTATGAAAAGTGAATTGGAATATGGTAACTGCA
9.VNHN3040805     AAATTGTCAAGAAAGGGGACTCAACAATTATGAAAAGTGAATTGGAATATGGTAACTGCA
VNJP1405          AAATTGTCAAGAAAGGGGACTCAACAATTATGAAAAGTGAATTGGAATATGGTAACTGCA
HK21303           AAATTGTCAAGAAAGGGGACTCAGCAATTATGAAAAGTGAATTGGAATATGGTAACTGCA
CkKoreaES03       AAATTGTCAAGAAAGGGGACTCAGCAATTATGAAAAGTGAATTGGAATATGGTAACTGCA
Indonesia505      AAATTGTCAAGAAAGGGGACTCAGCAATTATGAAAAGTGAATTGGAATATGGTAACTGCA
GsGuangdong196    AAATTGTCAAGAAAGGGGACTCAGCAATTATGAAAAGTGAATTGGAATATGGTAACTGCA
HK15697           AAATTGTCAAGAAAGGGGACTCAACAATTATGAAAAGTGAATTGGAATATGGTAACTGCA
HK48397           AAATTGTCAAGAAAGGGGACTCAACAATTATGAAAAGTGAATTGGAATATGGTAACTGCA
                  *********************** ************************************

VN120304          ACACCAAGTGTCAAACTCCAATGGGGGCGATAAA.CTCTAGCATGCCAT.TCCACAATATAC
```

Fig. 5B

```
10.VNHN3040805     ACACCAAGTGTCAA.ACACCAATGGGGGCGATAAA.TTCTAGTATGCCAT.TCCACAATATAC
VNJP1405           ACACCAAGTGTCAA.ACTCCAATGGGGGCGATAAA.CTCTAGTATGCCAC.TCCACAATATAC
HK21303            ACACCAAGTGTCAA.ACTCCAATGGGGGCGATAAA.CTCTAGTATGCCAT.TCCACAATATAC
CkKoreaES03        ACACCAAGTGTCAA.ACTCCAATGGGGGCGATAAA.CTCTAGTATGCCAT.TCCACAACATAC
Indonesia505       ACACCAAGTGTCAA.ACTCCAATGGGGGCGATAAA.CTCTAGTATGCCAT.TCCACAACATAC
GsGuangdong196     ACACCAAGTGTCAA.ACTCCAATGGGGGCGATAAA.CTCTAGTATGCCAT.TCCACAACATAC
HK15697            ACACCAAGTGTCAA.ACTCCAATGGGGGCGATAAA.CTCTAGTATGCCAT.TCCACAACATAC
HK48397            ACACCAAGTGTCAA.ACTCCAATGGGGGCGATAAA.CTCTAGTATGCCAT.TCCACAACATAC
                   ***************** ***************** ***** ****** ******* ****

VN120304           ACCCTCTCACCATTGGGGAATGCCCCAAATATGTGAAATCAAACAGATTAGTCCTTGCGA
11.VNHN3040805     ACCCTCTCACCATCGGGGAATGCCCCAAATATGTGAAATCAAACAGATTAGTCCTTGCGA
VNJP1405           ACCCTCTCACCATCGGGGAATGCCCCAAATATGTGAAATCAAACAGATTAGTCCTTGCGA
HK21303            ACCCTCTCACCATCGGGGAATGCCCCAAATATGTGAAATCAAACAGATTAGTCCTTGCGA
CkKoreaES03        ACCCTCTCACCATCGGGGAATGCCCCAAATATGTGAAATCAAGCAGATTAGTCCTTGCGA
Indonesia505       ACCCTCTCACCATCGGGGAATGCCCCAAATATGTGAAATCAAACAGATTAGTCCTTGCAA
GsGuangdong196     ACCCCCTCACCATCGGGGAATGCCCCAAATATGTGAAATCAAACAGATTAGTCCTTGCGA
HK15697            ACCCCCTCACCATCGGGGAATGCCCCAAATATGTGAAATCAAACAGATTAGTCCTTGCGA
HK48397            ACCCCCTCACCATCGGGGAATGCCCCAAATATGTGAAATCAAACAGATTAGTCCTTGCGA
                   **** ******** ***************************** *************** *

VN120304           CTGGGCTCA.GAAATAGCCCTCAAAGAGAG.AGAAGAAGAAAAAAGAGA.GGAT.TATTTGGAG
12.VNHN3040805     CTGGGCTCA.GAAATAGCCCTCAAAGAGAG.AGAAGAAA---AAGAGA.GGAT.TATTTGGAG
VNJP1405           CTGGGCTCA.GAAATAGCCCTCAAAGAGAG.AGAAGAAGAAAAAAGAGA.GGAT.TATTTGGAG
HK21303            CTGGGCTCA.GAAATAGCCCTCAAAGAGAG.AGAAGAAGAAAAAAGAGA.GGAT.TATTTGGAG
CkKoreaES03        CTGGGCTCA.GAAATAGCCCTCAAAGAGAG.---AAAAGAAAAAAGAGA.GGAC.TATTTGGAG
Indonesia505       CAGGGCTCA.GAAATAGCCCTCAAAGAGAG.AGCAGAAGAAAAAAGAGA.GGAC.TATTTGGAG
GsGuangdong196     CTGGACTCA.GAAATACCCCTCAAAGAGAG.AGAAGAAGAAAAAAGAGA.GGAC.TATTTGGAG
HK15697            CTGGACTCA.GAAATACCCCTCAAAGAGAG.AGAAGAAGAAAAAAGAGA.GGAC.TATTTGGAG
HK48397            CTGGACTCA.GAAATGCCCCTCAAAGAGAG.AGAAGAAGAAAAAAGAGA.GGAC.TATTTGGAG
                   * ** *********  *************   * ** *   ********* *********

VN120304           CTATAGCAGGT.TTTATAGAGGGA.GGATGGCAGGGAATGGTAGATGGTT
13.VNHN3040805     CTATAGCAGGT.TTTATAGAGGGA.GGATGGCAGGGAATGGTAGATGGTT
VNJP1405           CTATAGCAGGT.TTTATAGAGGGA.GGATGGCAGGGAATGGTAGATGGTT
HK21303            CTATAGCAGGT.TTTATAGAGGGA.GGATGGCAGGGAATGGTAGATGGTT
CkKoreaES03        CTATAGCAGGT.TTTATAGAGGGA.GGATGGCAGGGAATGGTAGATGGTT
Indonesia505       CTATAGCAGGT.TTTATAGAGGGA.GGATGGCAGGGAATGGTAGATGGTT
GsGuangdong196     CTATAGCAGGT.TTTATAGAGGGA.GGATGGCAGGGAATGGTAAATGGTT
HK15697            CTATAGCAGGT.TTTATAGAGGGA.GGATGGCAGGGAATGGTAGATGGTT
HK48397            CTATAGCAGGT.TTTATAGAGGGA.GGATGGCAGGGAATGGTAGATGGTT
                                       ++++
```

Fig. 5C

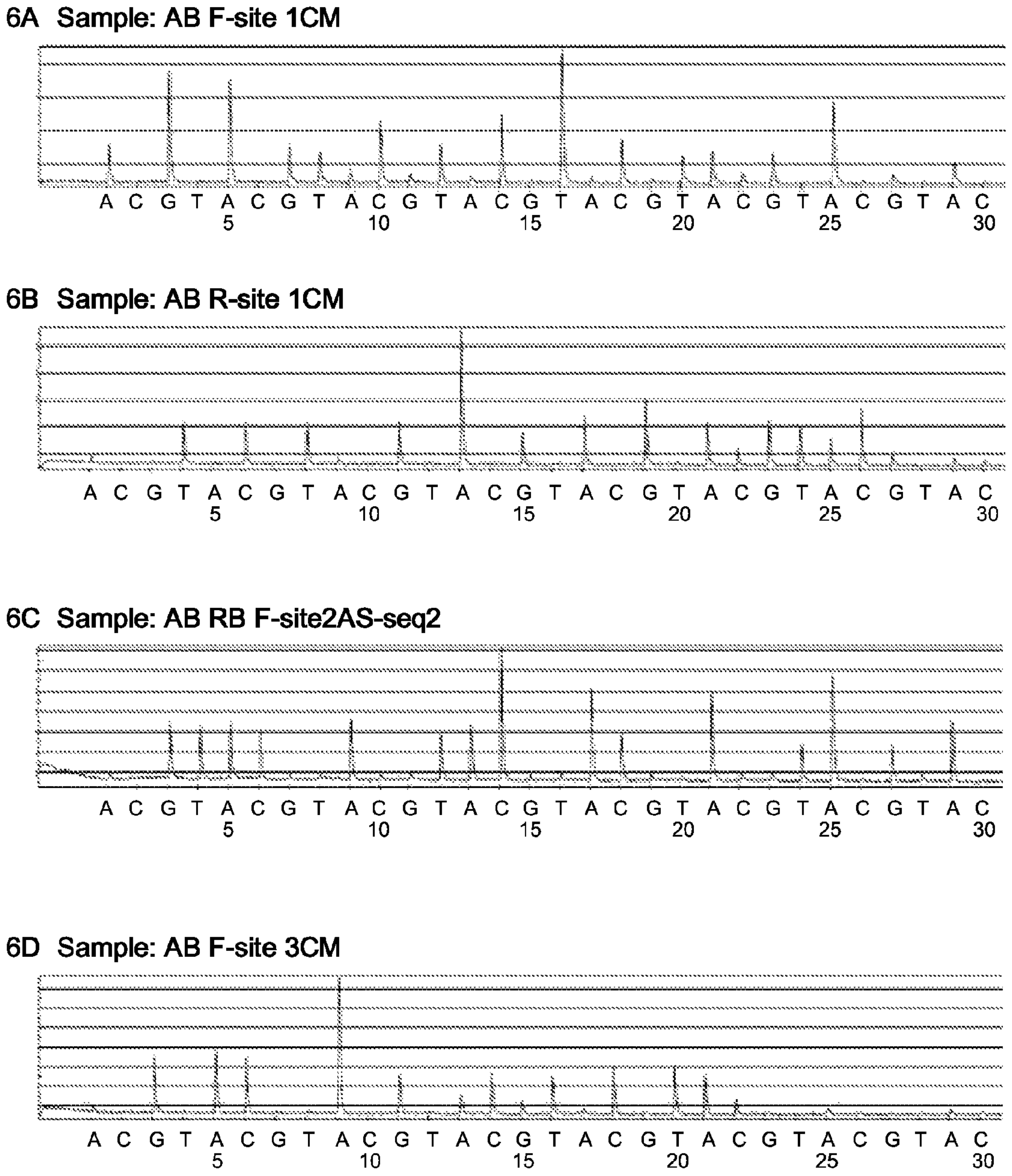
Fig. 6A-D

6E Sample: AB R-siteAS
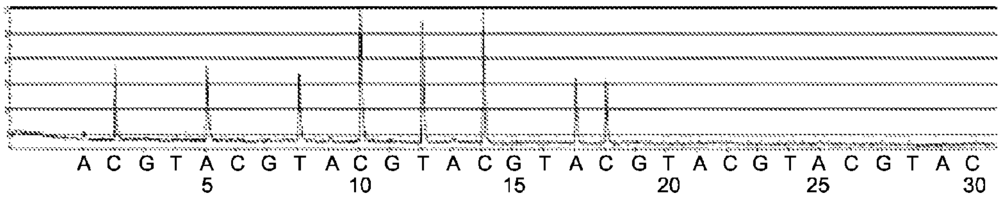
6F Sample: AB F-site 5CM
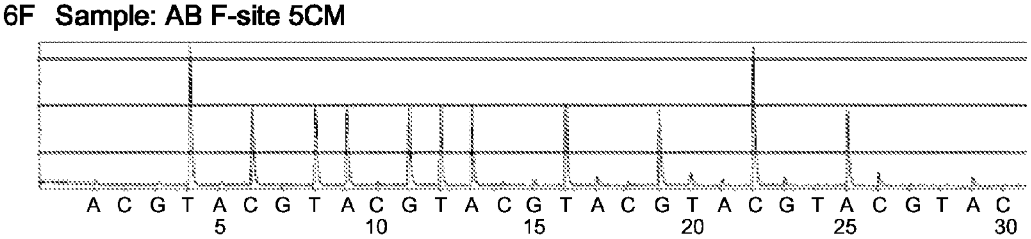
6G Sample: AB RB
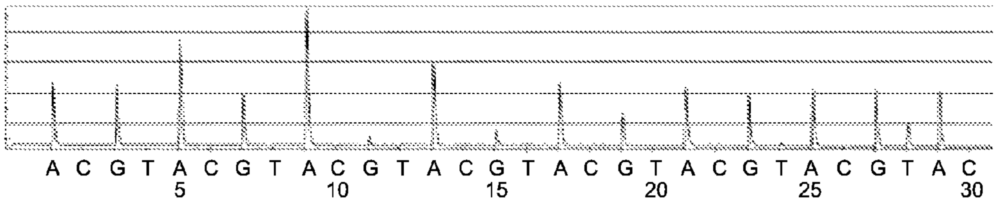
6H Sample: AB R-site6AS
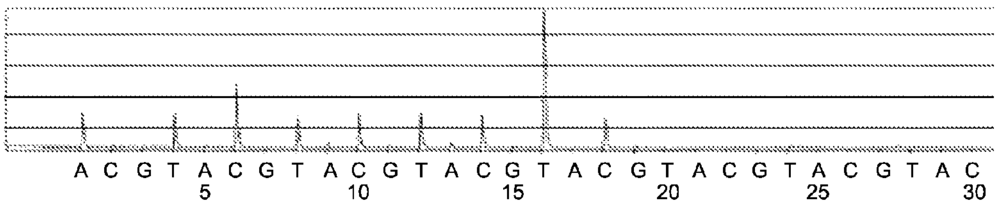
Fig. 6E-H 7A Sample: A9 F-site 1CM
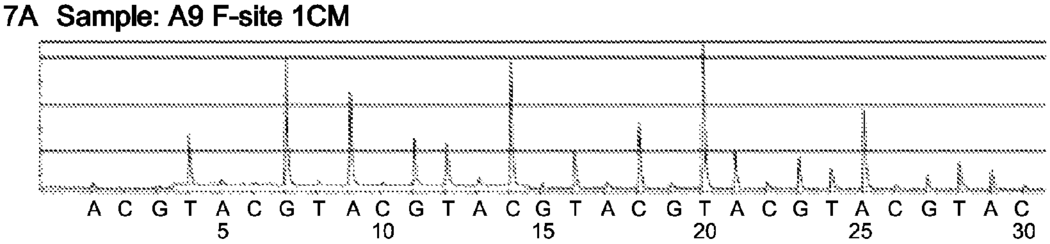
7B Sample: A9 R-site 1CM
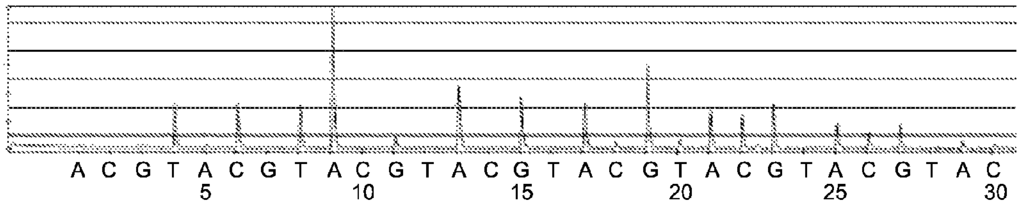
7C Sample: A9 RB F-site2AS-seq2
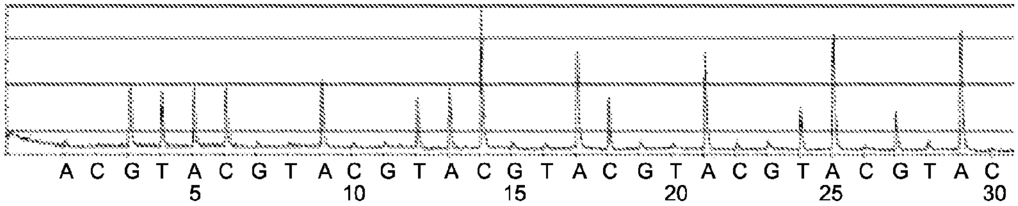
7D Sample: A9 F-site 3CM
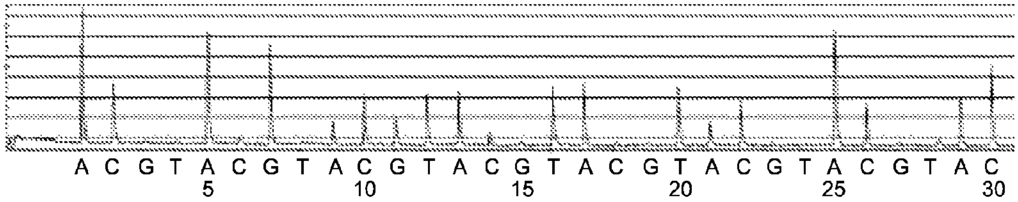
Fig. 7A-D

7E Sample: A9 R-site1AS
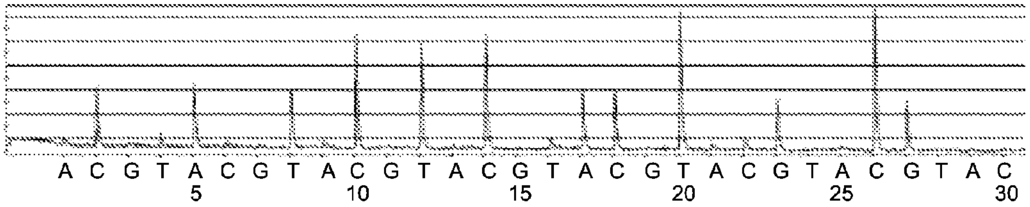
7F Sample: A9 F-site 5CM
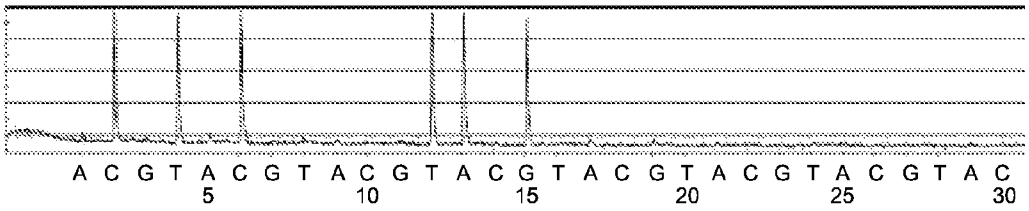
7G Sample: A9 RB
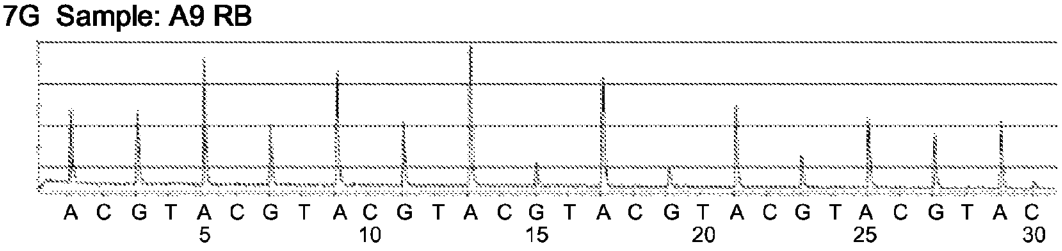
7H Sample: A9 R-site6AS
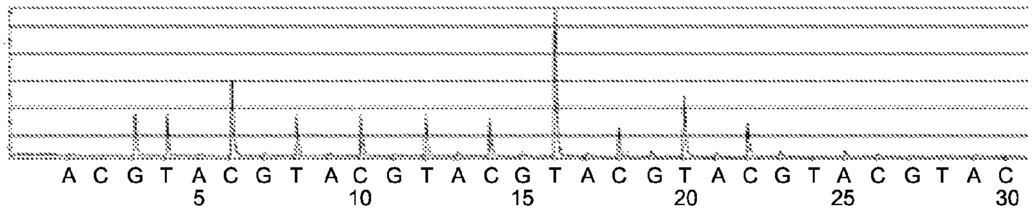
Fig. 7E-H 8A Sample: A10 F-site 1CM
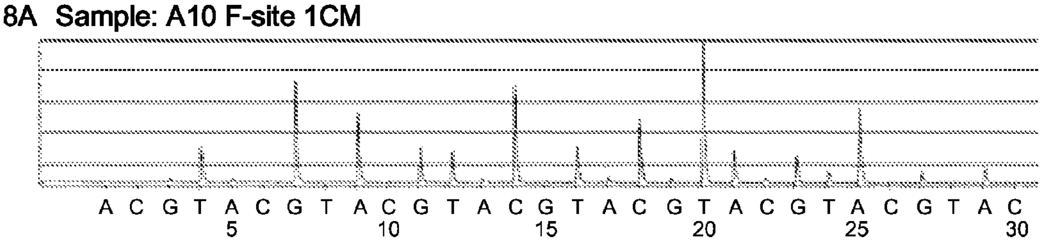
8B Sample: A10 R-site 1CM
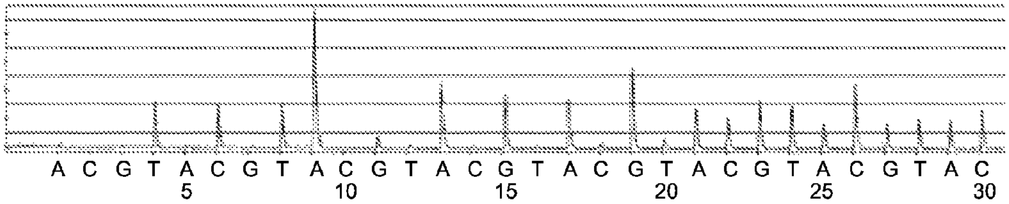
8C Sample: A10 RB F-site2AS-seq2
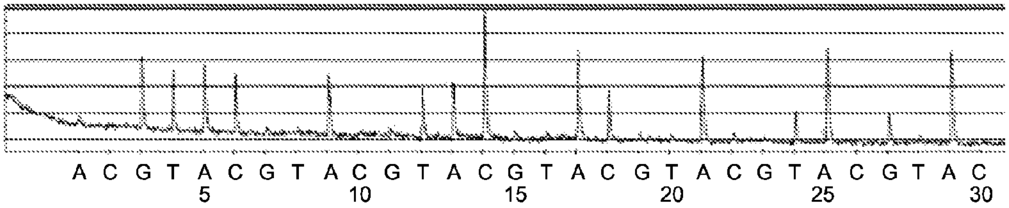
8D Sample: A10 F-site 3CM
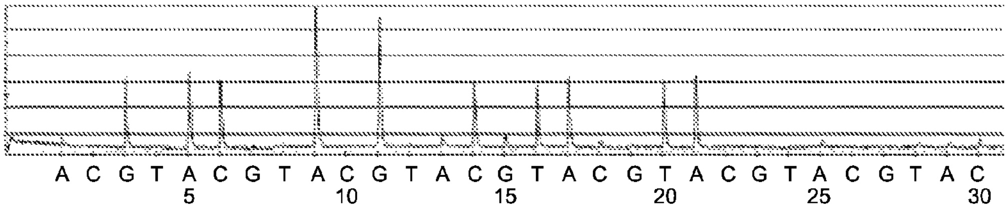
Fig. 8A-D 8E Sample: A10 R-site1AS
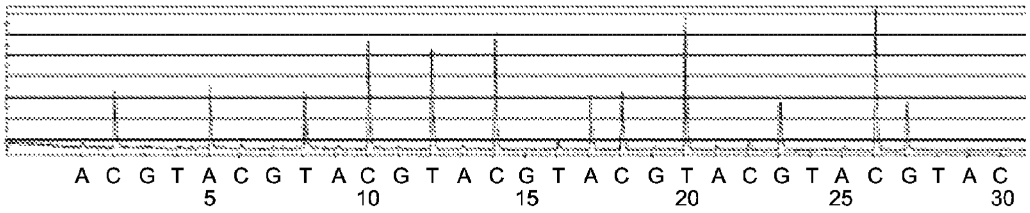
8F Sample: A10 F-site 5CM
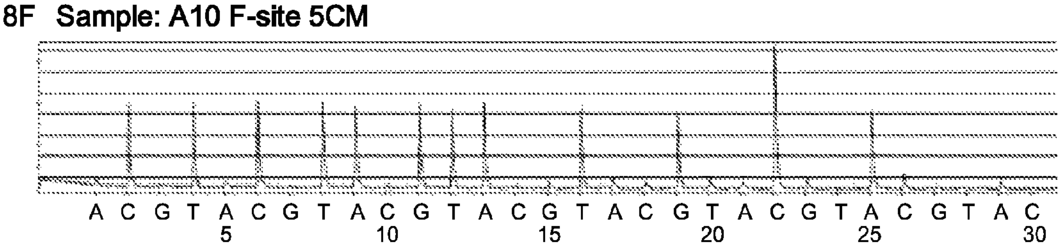
8G Sample: A10 RB
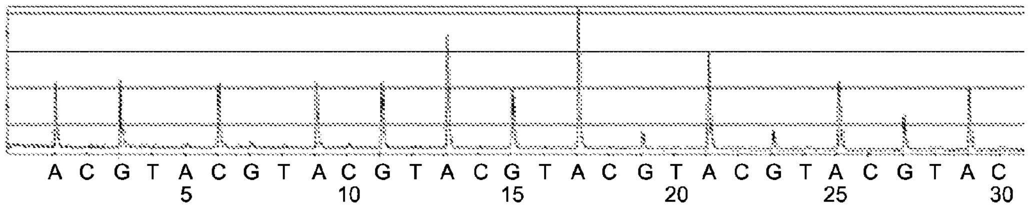
8H Sample: A10 R-site6AS
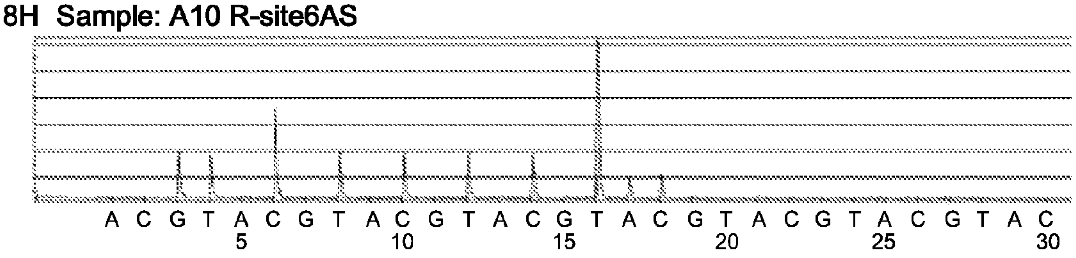
Fig. 8E-H

SEQUENCE LISTING

```
<160> NUMBER OF SEQ ID NOS: 88

<210> SEQ ID NO 1
<211> LENGTH: 564
<212> TYPE: PRT
<213> ORGANISM: Influenza A virus

<400> SEQUENCE: 1

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
```

-continued

```
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Gly Ser Trp Pro Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Lys Lys Arg Gly Leu Phe Gly Ala Ile Ala
            340                 345                 350

Gly Phe Ile Glu Gly Gly Trp Gln Gly Met Val Asp Gly Trp Tyr Gly
        355                 360                 365

Tyr His His Ser Asn Glu Gln Gly Ser Gly Tyr Ala Ala Asp Lys Glu
    370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
        435                 440                 445

Asn Glu Arg Thr Leu Asp Phe His Asp Ser Asn Val Lys Asn Leu Tyr
    450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Lys
            500                 505                 510
```

-continued

```
Leu Lys Arg Glu Glu Ile Ser Gly Val Lys Leu Glu Ser Ile Gly Ile
        515                 520                 525

Tyr Gln Ile Leu Ser Ile Tyr Ser Thr Val Ala Ser Ser Leu Ala Leu
    530                 535                 540

Ala Ile Met Val Ala Gly Leu Ser Leu Trp Met Cys Ser Asn Gly Ser
545                 550                 555                 560

Leu Gln Cys Arg


<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

agggaaagtc ctccttttc agaaa                                          25


<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

gtacataccc aacaata                                                  17


<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

gacaaagctc ta                                                       12


<210> SEQ ID NO 5
<211> LENGTH: 11
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

gtggaaggat g                                                        11


<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

ttctagtatg cca                                                      13


<210> SEQ ID NO 7
<211> LENGTH: 13
<212> TYPE: DNA
```

<213> ORGANISM: Artificial Sequence
<220> FEATURE:
<223> OTHER INFORMATION: Description of Artificial Sequence: Synthetic
primer

<400> SEQUENCE: 7
gaaaagagag gat 13

<210> SEQ ID NO 8
<211> LENGTH: 7
<212> TYPE: DNA
<213> ORGANISM: Artificial Sequence
<220> FEATURE:
<223> OTHER INFORMATION: Description of Artificial Sequence: Synthetic
primer

<400> SEQUENCE: 8 cgtccag 7

<210> SEQ ID NO 9
<211> LENGTH: 11
<212> TYPE: DNA
<213> ORGANISM: Artificial Sequence
<220> FEATURE:
<223> OTHER INFORMATION: Description of Artificial Sequence: Synthetic
primer

<400> SEQUENCE: 9
accaagaata g 11

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
primer

<400> SEQUENCE: 10
agagattggt accaag 16

<210> SEQ ID NO 11
<211> LENGTH: 19
<212> TYPE: DNA
<213> ORGANISM: Influenza A virus

<400> SEQUENCE: 11
gacaaagctc tatcaaaac 19

<210> SEQ ID NO 12
<211> LENGTH: 19
<212> TYPE: DNA
<213> ORGANISM: Influenza A virus

<400> SEQUENCE: 12
gacaaagcta tatcaaaac 19

<210> SEQ ID NO 13
<211> LENGTH: 768
<212> TYPE: DNA
<213> ORGANISM: Influenza A virus

<400> SEQUENCE: 13
tcaatgacta tgaagaattg aaacacctat tgagcagaat aaaccatttt gagaaaattc 60
agatcatccc caaaagttct tggtccagtc atgaagcctc attaggggtg agctcagcat 120

```
gtccatacca gggaaagtcc tcctttttca gaaatgtggt atggcttatc aaaaagaaca    180

gtacataccc aacaataaag aggagctaca ataataccaa ccaagaagat cttttggtac    240

tgtgggggat tcaccatcct aatgatgcgg cagagcagac aaagctctat caaaacccaa    300

ccacctatat ttccgttggg acatcaacac taaaccagag attggtacca agaatagcta    360

ctagatccaa agtaaacggg caaagtggaa ggatggagtt cttctggaca attttaaagc    420

cgaatgatgc aatcaacttc gagagtaatg gaaatttcat tgctccagaa tatgcataca    480

aaattgtcaa gaaaggggac tcaacaatta tgaaaagtga attggaatat ggtaactgca    540

acaccaagtg tcaaactcca atgggggcga taaactctag catgccattc cacaatatac    600

accctctcac cattggggaa tgccccaaat atgtgaaatc aaacagatta gtccttgcga    660

ctgggctcag aaatagccct caaagagaga gaagaagaaa aaagagagga ttatttggag    720

ctatagcagg ttttatagag ggaggatggc agggaatggt agatggtt                 768
```

<210> SEQ ID NO 14
<211> LENGTH: 765
<212> TYPE: DNA
<213> ORGANISM: Influenza A virus

<400> SEQUENCE: 14

```
tcaatgacta tgaagaattg aaacacttat tgagcagaat aaaccatttt gagaaaattc     60

agatcatccc caaaagttct tggcycagtc atgaagcctc attaggggtg agctcagcat    120

gtccatacca gggaaagtcc tcctttttca gaaatgtggt atggcttatc aaaaagaaca    180

gtacataccc aacaataaag aggagctaca ataacaccaa ccaagaagat ctgttggtac    240

tgtgggggat tcaccatcct aatgatgcgg cagagcagac aaagctctat caaaaaccaa    300

ccacctatat ttccgttggg acatcaacac taaaccagag attggtacca agaatagcta    360

ctagatccaa agtaaacggg caaagtggaa ggatggagtt cttctggaca attttaaaac    420

cgaatgatgc aatcaatttc gagagtaatg gaaatttcat tgccccagaa tatgcataca    480

aaattgtcaa gaaaggggac tcaacaatta tgaaaagtga attggaatat ggtaactgca    540

acaccaagtg tcaaacacca atgggggcga taaattctag tatgccattc cacaatatac    600

accctctcac catcggggaa tgccccaaat atgtgaaatc aaacagatta gtccttgcga    660

ctgggctcag aaatagccct caaagagaga gaagaaaaaa gagaggatta tttggagcta    720

tagcaggttt tatagaggga ggatggcagg gaatggtaga tggtt                    765
```

<210> SEQ ID NO 15
<211> LENGTH: 768
<212> TYPE: DNA
<213> ORGANISM: Influenza A virus

<400> SEQUENCE: 15

```
tcaatgacta tgaagaattg aaacacctat tgagcagaat aaaccatttt gagaaaattc     60

agatcatccc caaaagttct tggtccagtc atgaagcctc attgggggtg agcgcagcat    120

gtccatacca gggaaagtcc tcctttttca gaaatgtggt atggcttatc aaaaagaaca    180

gtacataccc aacaataaag aggagctaca ataataccaa ccaagaagat cttttggtaa    240

tgtgggggat ccaccatcct aatgatgcgg cagagcagac aaagctctat caaaacccaa    300

ccacctatat ttccgttggg acatcaacac taaaccagag attggtacca agaatagcta    360

ctagatccaa agtaaacggg caaagtggga ggatggagtt cttctggaca attttaaaac    420

cgaatgatgc aatcaacttc gagagtaatg gaaatttcat tgctccagaa tatgcataca    480
```

-continued

```
aaattgtcaa gaaaggggac tcaacaatta tgaaaagtga attggaatat ggtaactgca    540

acaccaagtg tcaaactcca atgggggcga taaactctag tatgccactc cacaatatac    600

accctctcac catcggggaa tgccccaaat atgtgaaatc aaacagatta gtccttgcga    660

ctgggctcag aaatagccct caaagagaga gaagaagaaa aaagagagga ttatttggag    720

ctatagcagg ttttatagag ggaggatggc agggaatggt agatggtt                768
```

<210> SEQ ID NO 16
<211> LENGTH: 768
<212> TYPE: DNA
<213> ORGANISM: Influenza A virus

<400> SEQUENCE: 16

```
tcaacgacta tgaagaattg aaacacctat tgagcagaat aaaccatttt gagaaaattc     60

agatcatccc caaaaattct tggtccagtc atgaagcctc attaggggtg agctcagcat    120

gtccatacca aggaaagtcc tcctttttca ggaatgtggt atggcttatc aaaaagaaca    180

atgcataccc aacaataaag aggagctaca ataataccaa ccaagaagat cttttggtat    240

tgtgggggat tcaccatcct aatgatgcgg cagagcagac taggctctat caaaacccaa    300

ccacctacat ttccgttggg acatcaacac taaaccagag attggtacca aaaatagcta    360

ctagatccaa agtaaacggg caaaatggaa ggatggagtt cttctggaca attttaaaac    420

cgaatgatgc aatcaacttc gagagcaatg gaaatttcat tgctccagaa tatgcataca    480

aaattgtcaa gaaaggggac tcagcaatta tgaaaagtga attggaatat ggtaactgca    540

acaccaagtg tcaaactcca atgggggcga taaactctag tatgccattc cacaatatac    600

accctctcac catcggggaa tgccccaaat atgtgaaatc aaacagatta gtccttgcga    660

ctgggctcag aaatagccct caaagagaga gaagaagaaa aaagagagga ttatttggag    720

ctatagcagg ttttatagag ggaggatggc agggaatggt agatggtt                768
```

<210> SEQ ID NO 17
<211> LENGTH: 765
<212> TYPE: DNA
<213> ORGANISM: Influenza A virus

<400> SEQUENCE: 17

```
tcaacgacta tgaagaactg aaacacctat tgagcagaat aaaccatttt gaaaaaattc     60

agatcatccc caaaagttct tggtccgatc atgaagcctc atcaggggtg agctcagcat    120

gtccatacca gggaaggtcc tccttcttca gaaatgtggt atggcttatc aaaaagaaca    180

gtgcataccc aacaataaag agaagctaca ataataccaa ccaagaagat cttttggtac    240

tgtgggggat tcaccatcca aatgatgcgg cagagcagac aagactctat caaaacccaa    300

ccacctatat ttccgttggg acatcaacac taaaccagag attggtacca aaaatagcta    360

ctagatccaa agtaaacggg caaagtggaa ggatggagtt cttctggaca attttaaaac    420

cgaatgatgc aatcagcttt gagagtaatg gaaatttcat tgctccagaa tatgcataca    480

aaattgtcaa gaaaggggac tcagcaatta tgaaaagtga attggaatat ggtaactgca    540

acaccaagtg tcaaactcca atgggggcga taaactctag tatgccattc cacaacatac    600

accctctcac catcggggaa tgccccaaat atgtgaaatc aagcagatta gtccttgcga    660

ctgggctcag aaatagccct caaagagaga aaagaaaaaa gagaggacta tttggagcta    720

tagcaggttt tatagaggga ggatggcagg gaatggtaga tggtt                   765
```

<210> SEQ ID NO 18

<211> LENGTH: 768
<212> TYPE: DNA
<213> ORGANISM: Influenza A virus

<400> SEQUENCE: 18

```
tcaacgacta tgaagaactg aaacacctat tgagcagaat aaaccatttt gagaaaattc     60

aaatcatccc caaaagttct tggtccgatc atgaagcctc atcaggagtg agctcagcat    120

gtccatacct gggaagtccc tcctttttta gaaatgtggt atggcttatc aaaaagaaca    180

gtacataccc aacaataaag aaaagctaca ataataccaa ccaagaagat cttttggtac    240

tgtggggaat tcaccatcct aatgatgcgg cagagcagac aaggctatat caaaacccaa    300

ccacctatat ttccattggg acatcaacac taaaccagag attggtacca aaaatagcta    360

ctagatccaa agtaaacggg caaagtggaa ggatggagtt cttctggaca attttaaaac    420

ctaatgatgc aatcaacttc gagagtaatg gaaatttcat tgctccagaa tatgcataca    480

aaattgtcaa gaaaggggac tcagcaatta tgaaaagtga attggaatat ggtaactgca    540

acaccaagtg tcaaactcca atgggggcga taaactctag tatgccattc cacaacatac    600

accctctcac catcggggaa tgccccaaat atgtgaaatc aaacagatta gtccttgcaa    660

cagggctcag aaatagccct caaagagaga gcagaagaaa aaagagagga ctatttggag    720

ctatagcagg ttttatagag ggaggatggc agggaatggt agatggtt                 768
```

<210> SEQ ID NO 19
<211> LENGTH: 768
<212> TYPE: DNA
<213> ORGANISM: Influenza A virus

<400> SEQUENCE: 19

```
tcaacgacta tgaagaactg aaacacctat tgagcagaac aaaccatttt gagaagattc     60

agatcatccc cccaagttct tggtccaatc atgatgcctc atcaggggtg agctcagcat    120

gtccatacca tgggaggtcc tcctttttca gaaatgtggt atggcttatc aaaaagaaca    180

gtgcataccc aacaataaag aggagctaca ataataccaa ccaagaagat cttttagtac    240

tgtgggggat tcaccatcct aatgatgcgg cagagcagac aaagctatat caaaacccaa    300

ccacttacat ttccgttgga acatcaacac tgaaccagag attggttcca gaaatagcta    360

ctagacccaa agtaaacggg caaagtggaa gaatggagtt cttctggaca attttaaagc    420

cgaatgatgc catcaatttc gagagtaatg gaaatttcat tgctccagaa tatgcataca    480

aaattgtcaa gaaaggggac tcagcaatta tgaaaagtga attggaatat ggtaactgca    540

acaccaagtg tcaaactcca atgggggcga taaactctag tatgccattc cacaacatac    600

accccctcac catcggggaa tgccccaaat atgtgaaatc aaacagatta gtccttgcga    660

ctggactcag aaataccccct caaagagaga gaagaagaaa aaagagagga ctatttggag    720

ctatagcagg ttttatagag ggaggatggc agggaatggt aaatggtt                 768
```

<210> SEQ ID NO 20
<211> LENGTH: 768
<212> TYPE: DNA
<213> ORGANISM: Influenza A virus

<400> SEQUENCE: 20

```
tcaacgacta tgaagaactg aaacacctat tgagcagaat aaaccatttt gagaaaatcc     60

agatcatccc caaaagttct tggtccaatc atgatgcctc atcaggggtg agctcagcat    120

gtccatacct tgggaggtcc tcctttttca gaaatgtggt atggcttatc aaaaagaaca    180
```

-continued

```
gtgcataccc aacaataaag aggagctaca ataataccaa ccaagaagat cttttggtac    240

tgtgggggat tcaccatcct aatgatgcgg cagagcagac aaagctctat caaaatccaa    300

ccacctacat ttccgttgga acatcaacac tgaaccagag attggttcca gaaatagcta    360

ctagacccaa agtaaacggg caaagtggaa gaatggagtt cttctggaca attttaaagc    420

cgaatgatgc catcaatttc gagagtaatg gaaatttcat tgctccagaa tatgcataca    480

aaattgtcaa gaaaggggac tcaacaatta tgaaaagtga attggaatat ggtaactgca    540

acaccaagtg tcaaactcca atgggggcga taaactctag tatgccattc cacaacatac    600

acccccctcac catcggggaa tgccccaaat atgtgaaatc aaacagatta gtccttgcga    660

ctggactcag aaataccccct caaagagaga gaagaagaaa aaagagagga ctatttggag    720

ctatagcagg ttttatagag ggaggatggc agggaatggt agatggtt                 768


<210> SEQ ID NO 21
<211> LENGTH: 768
<212> TYPE: DNA
<213> ORGANISM: Influenza A virus

<400> SEQUENCE: 21

tcaacgacta tgaagaactg aaacacctat tgagcagaat aaaccatttt gagaaaattc     60

agatcatccc caaaagttct tggtccaatc atgatgcctc atcaggggta agctcagcat    120

gtccatacct tgggaagtcc tcctttttca gaaatgtggt atggcttatc aaaaagaaca    180

gtacataccc aacaataaag aggagctaca ataataccaa ccaagaagat cttttggtac    240

tgtgggggat tcaccatcct aatgatgcgg cagagcagac aaagctctat caaaacccaa    300

ccacctacat ttccgttgga acatcaacac tgaaccagag attggttcca gaaatagcta    360

ctagacccaa agtaaacggg caaagtggaa gaatagagtt cttctggaca attttaaagc    420

cgaatgatgc catcaatttc gagagtaatg gaaatttcat tgctccagaa tatgcataca    480

aaattgtcaa gaaaggggac tcaacaatta tgaaaagtga attggaatat ggtaactgca    540

acaccaagtg tcaaactcca atgggggcga taaactctag tatgccattc cacaacatac    600

acccccctcac catcggggaa tgccccaaat atgtgaaatc aaacagatta gtccttgcga    660

ctggactcag aaatgcccct caaagagaga gaagaagaaa aaagagagga ctatttggag    720

ctatagcagg ttttatagag ggaggatggc agggaatggt agatggtt                 768


<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

tcaatgacta tgaagaattg aaaca                                           25


<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

aaccatctac cattccctgc catcc                                           25
```

-continued

<210> SEQ ID NO 24
<211> LENGTH: 6
<212> TYPE: PRT
<213> ORGANISM: Influenza A virus

<400> SEQUENCE: 24

Ser Arg Arg Lys Lys Arg
1               5

<210> SEQ ID NO 25
<211> LENGTH: 23
<212> TYPE: DNA
<213> ORGANISM: Influenza A virus

<400> SEQUENCE: 25
aacctggttc ttgaaaccca tca 23

<210> SEQ ID NO 26
<211> LENGTH: 22
<212> TYPE: DNA
<213> ORGANISM: Influenza A virus

<400> SEQUENCE: 26
gacctggttc ttaaacccat ca 22

<210> SEQ ID NO 27
<211> LENGTH: 23
<212> TYPE: DNA
<213> ORGANISM: Influenza A virus

<400> SEQUENCE: 27
agcctggttc ttgaaaccca tca 23

<210> SEQ ID NO 28
<211> LENGTH: 23
<212> TYPE: DNA
<213> ORGANISM: Influenza A virus

<400> SEQUENCE: 28
gacctggttc ttgaaaccca tca 23

<210> SEQ ID NO 29
<211> LENGTH: 12
<212> TYPE: DNA
<213> ORGANISM: Influenza A virus

<400> SEQUENCE: 29
gacctcggtc tt 12

<210> SEQ ID NO 30
<211> LENGTH: 24
<212> TYPE: DNA
<213> ORGANISM: Influenza A virus

<400> SEQUENCE: 30
cagcctggtt cttgaaaccc atca 24

<210> SEQ ID NO 31
<211> LENGTH: 24
<212> TYPE: DNA
<213> ORGANISM: Influenza A virus

<400> SEQUENCE: 31
cagcctggtt cttgaaaggg atca 24

<210> SEQ ID NO 32
<211> LENGTH: 26
<212> TYPE: DNA
<213> ORGANISM: Influenza A virus

<400> SEQUENCE: 32
atgggaggtc ctcctttttt cagaaa 26

<210> SEQ ID NO 33
<211> LENGTH: 23
<212> TYPE: DNA
<213> ORGANISM: Influenza A virus

<400> SEQUENCE: 33
ttgggaggtc ctcctttttc aga 23

<210> SEQ ID NO 34
<211> LENGTH: 23
<212> TYPE: DNA
<213> ORGANISM: Influenza A virus

<400> SEQUENCE: 34
ttgggaagtc ctcctttttc aga 23

<210> SEQ ID NO 35
<211> LENGTH: 22
<212> TYPE: DNA
<213> ORGANISM: Influenza A virus

<400> SEQUENCE: 35
aaggaaagtc ctcctttttc ag 22

<210> SEQ ID NO 36
<211> LENGTH: 25
<212> TYPE: DNA
<213> ORGANISM: Influenza A virus

<400> SEQUENCE: 36
agggaaggtc ctccttcttc agaaa 25

<210> SEQ ID NO 37
<211> LENGTH: 24
<212> TYPE: DNA
<213> ORGANISM: Influenza A virus

<400> SEQUENCE: 37
agggaaaagt cctccttttt caga 24

<210> SEQ ID NO 38
<211> LENGTH: 25
<212> TYPE: DNA
<213> ORGANISM: Influenza A virus

<400> SEQUENCE: 38
agggaaagtc ctcctttttc agaaa 25

<210> SEQ ID NO 39
<211> LENGTH: 23
<212> TYPE: DNA
<213> ORGANISM: Influenza A virus

<400> SEQUENCE: 39
tgggaagtcc ctcctttttt aga 23

<210> SEQ ID NO 40
<211> LENGTH: 19
<212> TYPE: DNA
<213> ORGANISM: Influenza A virus

<400> SEQUENCE: 40
gtgcataccc aacaataaa 19

<210> SEQ ID NO 41
<211> LENGTH: 21
<212> TYPE: DNA
<213> ORGANISM: Influenza A virus

<400> SEQUENCE: 41
gtacataccc aacaataaag a 21

<210> SEQ ID NO 42
<211> LENGTH: 18
<212> TYPE: DNA
<213> ORGANISM: Influenza A virus

<400> SEQUENCE: 42
atgcataccc aacaataa 18

<210> SEQ ID NO 43
<211> LENGTH: 20
<212> TYPE: DNA
<213> ORGANISM: Influenza A virus

<400> SEQUENCE: 43
gtgcactacc caacaataaa 20

<210> SEQ ID NO 44
<211> LENGTH: 22
<212> TYPE: DNA
<213> ORGANISM: Influenza A virus

<400> SEQUENCE: 44
gtacatacca acaataaaga aa 22

<210> SEQ ID NO 45
<211> LENGTH: 20
<212> TYPE: DNA
<213> ORGANISM: Influenza A virus

<400> SEQUENCE: 45
gtacataccc aacaataaga 20

<210> SEQ ID NO 46
<211> LENGTH: 22
<212> TYPE: DNA
<213> ORGANISM: Influenza A virus

<400> SEQUENCE: 46
gtacataccc aacaataaag aa 22

<210> SEQ ID NO 47
<211> LENGTH: 12
<212> TYPE: DNA
<213> ORGANISM: Influenza A virus

<400> SEQUENCE: 47
gacaaagctc ta 12

<210> SEQ ID NO 48
<211> LENGTH: 12
<212> TYPE: DNA
<213> ORGANISM: Influenza A virus

<400> SEQUENCE: 48
gacaagactc ta 12

<210> SEQ ID NO 49
<211> LENGTH: 12
<212> TYPE: DNA
<213> ORGANISM: Influenza A virus

<400> SEQUENCE: 49
gacaaggcta ta 12

<210> SEQ ID NO 50
<211> LENGTH: 24
<212> TYPE: DNA
<213> ORGANISM: Influenza A virus

<400> SEQUENCE: 50
taccagaaat agctactaga ccaa 24

<210> SEQ ID NO 51
<211> LENGTH: 11
<212> TYPE: DNA
<213> ORGANISM: Influenza A virus

<400> SEQUENCE: 51
tccagaaata g 11

<210> SEQ ID NO 52
<211> LENGTH: 8
<212> TYPE: DNA
<213> ORGANISM: Influenza A virus

<400> SEQUENCE: 52 accaaaaa 8

<210> SEQ ID NO 53
<211> LENGTH: 9
<212> TYPE: DNA
<213> ORGANISM: Influenza A virus

<400> SEQUENCE: 53 accaaagaa 9

<210> SEQ ID NO 54
<211> LENGTH: 8
<212> TYPE: DNA
<213> ORGANISM: Influenza A virus

<400> SEQUENCE: 54 accaagaa 8

<210> SEQ ID NO 55
<211> LENGTH: 9
<212> TYPE: DNA
<213> ORGANISM: Influenza A virus

<400> SEQUENCE: 55 accgaagaa 9

<210> SEQ ID NO 56
<211> LENGTH: 11
<212> TYPE: DNA
<213> ORGANISM: Influenza A virus

<400> SEQUENCE: 56
agaccttggt t 11

<210> SEQ ID NO 57
<211> LENGTH: 16
<212> TYPE: DNA
<213> ORGANISM: Influenza A virus

<400> SEQUENCE: 57
agaccttggt tagaga 16

<210> SEQ ID NO 58
<211> LENGTH: 12
<212> TYPE: DNA
<213> ORGANISM: Influenza A virus

<400> SEQUENCE: 58
agacctttgg tt 12

<210> SEQ ID NO 59
<211> LENGTH: 26
<212> TYPE: DNA
<213> ORGANISM: Influenza A virus

<400> SEQUENCE: 59
aaaccatggt tagagaccaa atcaca 26

<210> SEQ ID NO 60
<211> LENGTH: 19
<212> TYPE: DNA
<213> ORGANISM: Influenza A virus

<400> SEQUENCE: 60
aaaccatggt tagagacaa 19

<210> SEQ ID NO 61
<211> LENGTH: 11
<212> TYPE: DNA
<213> ORGANISM: Influenza A virus

<400> SEQUENCE: 61
gaaacccatg g 11

<210> SEQ ID NO 62
<211> LENGTH: 24
<212> TYPE: DNA
<213> ORGANISM: Influenza A virus

<400> SEQUENCE: 62
gaaacccatg gttagagacc aaat 24

<210> SEQ ID NO 63
<211> LENGTH: 5
<212> TYPE: DNA
<213> ORGANISM: Influenza A virus

<400> SEQUENCE: 63 aaacc 5

<210> SEQ ID NO 64
<211> LENGTH: 33
<212> TYPE: DNA
<213> ORGANISM: Influenza A virus

<400> SEQUENCE: 64
gtaagaaggt gaaacgggca aatgaaaccc aga 33

<210> SEQ ID NO 65
<211> LENGTH: 25
<212> TYPE: DNA
<213> ORGANISM: Influenza A virus

<400> SEQUENCE: 65
gtaagaaggt ggaaacgggc aaatg 25

<210> SEQ ID NO 66
<211> LENGTH: 19
<212> TYPE: DNA
<213> ORGANISM: Influenza A virus

<400> SEQUENCE: 66
ataagaaggt gaaacgggc 19

<210> SEQ ID NO 67
<211> LENGTH: 15
<212> TYPE: DNA
<213> ORGANISM: Influenza A virus

<400> SEQUENCE: 67
gtaggaaggt aaaac 15

<210> SEQ ID NO 68
<211> LENGTH: 20
<212> TYPE: DNA
<213> ORGANISM: Influenza A virus

<400> SEQUENCE: 68
gtaggaaggt gaaacgggca 20

<210> SEQ ID NO 69
<211> LENGTH: 20
<212> TYPE: DNA
<213> ORGANISM: Influenza A virus

<400> SEQUENCE: 69
gtaggaaggt gaaacggggc 20

<210> SEQ ID NO 70
<211> LENGTH: 19
<212> TYPE: DNA
<213> ORGANISM: Influenza A virus

<400> SEQUENCE: 70
gtaggagggt gaaacgggc 19

<210> SEQ ID NO 71
<211> LENGTH: 11
<212> TYPE: DNA
<213> ORGANISM: Influenza A virus

<400> SEQUENCE: 71
gtaggaaggt g 11

<210> SEQ ID NO 72
<211> LENGTH: 19
<212> TYPE: DNA
<213> ORGANISM: Influenza A virus

<400> SEQUENCE: 72
gtaggaaggt gaaacgggc 19

<210> SEQ ID NO 73
<211> LENGTH: 13
<212> TYPE: DNA
<213> ORGANISM: Influenza A virus

<400> SEQUENCE: 73
ctctagtatg cca 13

<210> SEQ ID NO 74
<211> LENGTH: 8
<212> TYPE: DNA
<213> ORGANISM: Influenza A virus

<400> SEQUENCE: 74 ctctagta 8

<210> SEQ ID NO 75
<211> LENGTH: 13
<212> TYPE: DNA
<213> ORGANISM: Influenza A virus

<400> SEQUENCE: 75
ctctagcatg cca 13

<210> SEQ ID NO 76
<211> LENGTH: 14
<212> TYPE: DNA
<213> ORGANISM: Influenza A virus

<400> SEQUENCE: 76
ctctagtatg ccac 14

<210> SEQ ID NO 77
<211> LENGTH: 13
<212> TYPE: DNA
<213> ORGANISM: Influenza A virus

<400> SEQUENCE: 77
ttctagtatg cca 13

<210> SEQ ID NO 78
<211> LENGTH: 23
<212> TYPE: DNA
<213> ORGANISM: Influenza A virus

<400> SEQUENCE: 78
agaagaagaa aaaagagaga gga 23

<210> SEQ ID NO 79
<211> LENGTH: 18
<212> TYPE: DNA
<213> ORGANISM: Influenza A virus

<400> SEQUENCE: 79
agaagaagaa aaaagaga 18

-continued

<210> SEQ ID NO 80
<211> LENGTH: 21
<212> TYPE: DNA
<213> ORGANISM: Influenza A virus

<400> SEQUENCE: 80
agaagaagaa aaaagagagg a 21

<210> SEQ ID NO 81
<211> LENGTH: 15
<212> TYPE: DNA
<213> ORGANISM: Influenza A virus

<400> SEQUENCE: 81
aaaagaaaaa agaga 15

<210> SEQ ID NO 82
<211> LENGTH: 17
<212> TYPE: DNA
<213> ORGANISM: Influenza A virus

<400> SEQUENCE: 82
agaagaaaaa agagagg 17

<210> SEQ ID NO 83
<211> LENGTH: 18
<212> TYPE: DNA
<213> ORGANISM: Influenza A virus

<400> SEQUENCE: 83
agcagaagaa aaaagaga 18

<210> SEQ ID NO 84
<211> LENGTH: 4
<212> TYPE: PRT
<213> ORGANISM: Influenza A virus

<400> SEQUENCE: 84

Gly Gln Ser Gly
1

<210> SEQ ID NO 85
<211> LENGTH: 4
<212> TYPE: PRT
<213> ORGANISM: Influenza A virus

<400> SEQUENCE: 85

Gly Gln Asn Gly
1

<210> SEQ ID NO 86
<211> LENGTH: 6
<212> TYPE: PRT
<213> ORGANISM: Influenza A virus

<400> SEQUENCE: 86

Arg Arg Arg Lys Lys Arg
1 5

<210> SEQ ID NO 87
<211> LENGTH: 5
<212> TYPE: PRT
<213> ORGANISM: Influenza A virus -continued

```
<400> SEQUENCE: 87

Arg Arg Lys Lys Arg
1               5


<210> SEQ ID NO 88
<211> LENGTH: 5
<212> TYPE: PRT
<213> ORGANISM: Influenza A virus

<400> SEQUENCE: 88

Lys Arg Lys Lys Arg
1               5
```

RAPID, INFORMATIVE DIAGNOSTIC ASSAY FOR INFLUENZA VIRUSES INCLUDING H5N1

CROSS-REFERENCE TO RELATED APPLICATIONS

This application claims priority from U.S. Provisional Patent Application No. 60/861,603 filed on Nov. 29, 2006, which is hereby incorporated by reference in its entirety.

STATEMENT OF GOVERNMENTAL SUPPORT

This invention was made with U.S. Government support under National Institutes of Health Grants 1R21 A1059499-01 and PO1-HG000205. The U.S. Government has certain rights in this invention.

REFERENCE TO SEQUENCE LISTING, COMPUTER PROGRAM, OR COMPACT DISK

Applicants assert that the paper copy of the Sequence Listing is identical to the Sequence Listing in computer readable form found on the accompanying computer disk. Applicants incorporate the contents of the sequence listing by reference in its entirety.

BACKGROUND OF THE INVENTION

1. Field of the Invention

The present invention relates to the field of nucleic acid diagnostics, and, in particular to devices and methods for identification of viral pathogens such as avian influenza, by nucleic acid sequencing.

2. Related Art

INTRODUCTION

The worldwide spread of high pathogenicity H5N1 avian influenza A virus in poultry and wild birds has resulted in many human infections, with high fatality rates. Although sustained transmission human-to-human has not yet occurred, concern about a potential pandemic continues to mount. The avian influenza A subtype H5N1 was first found among domestic poultry populations in 1996 in southern China (Xu et al., 1999). A similar H5N1 influenza virus spread directly from poultry to humans in Hong Kong in 1997, causing the deaths in 6 of 18 persons diagnosed with infection with this virus (Subbarao et al., 1998). While eradicated in Hong Kong through massive culling of poultry, the disease has continued to spread across Asia, causing human deaths in Thailand, Vietnam, Indonesia, China and elsewhere (Subbarao et al., 1998). The rapid spread of H5N1 from Asia into Europe and Africa in recent months has intensified efforts to control the virus and avert a pandemic. To address the recognized need for rapid, low-cost diagnosis, tracking critically important genetic changes in the virus among animal and human host populations, and identifying specific viral clades (WHO 2005), there is described below high-throughput methods for monitoring viral mutations that may control virulence and transmissibility in humans (Shinya et al., 2005). Accurate and rapid detection and tracking of H5N1 will be critical to prevent or control a potential pandemic.

Diagnosis of influenza type A infections in clinical microbiology laboratories has traditionally been performed using cell culture and/or direct fluorescent antibody assays (Schmidt et al., 1989; Effler et al., 2002; Shinya et al., 2005). These methods are time-consuming and require biosafety level 3 (–) biocontainment facilities and equipment to protect laboratory personnel from exposure to H5N1 cultured in the laboratory. Because these facilities are not widely available, culture-based assays are increasingly being replaced in clinical settings by the various polymerase chain reaction (PCR) methods (Fan et al., 1998; Habib-Bein et al., 2003; Templeton et al., 2004; Whiley and Sloots 2005).

PCR is more sensitive than traditional tests and detection does not require viable virus or morphologically intact infected cells in the sample. The PCR-based molecular diagnostic test is currently the most widely used to diagnose the presence of H5N1 in clinical specimens ((CDC) 2006). As described below, coupling a PCR assay to a rapid sequencing method would further increase the value of molecular techniques for virus identification, especially if implemented into automated robotic platforms. Nucleic acid sequencing is considered the most reliable and highest-resolution method for virus identification, but is typically considered to be too slow and costly to use as a primary assay. Samples can be prepared sequentially for PCR diagnosis of H5N1 influenza virus, and pyrosequencing, yielding results in approximately 90 minutes, with immediate availability of the viral sequence data. The speed, sensitivity, precision, low cost, and high throughput of this method give it substantial advantages in H5N1 influenza detection.

Influenza type A viruses have an eight-segment negative-sense RNA genome complexed with nucleoprotein and polymerase surrounded by the matrix protein and a lipid envelope that contains two integral membrane glycoproteins, hemagglutinin (HA) and neuraminidase (NA), protruding from the virion surface. Described below is an assay that focuses on three biologically significant regions of the H5N1 hemagglutinin gene (HA gene), including sites informative of viral ancestry.

As described further below, these sites are:

(1) glycosylation sites at amino acid residues 154-156;

(2) the receptor-binding site at amino acid residues 221-224; and (3) the cleavage motif at amino acid residues 325-329.

Amino acid numbering may be further identified with reference to GenBank locus ABE97594, containing the amino acid sequence of the Influenza A virus A/duck/Vietnam/317/2005(H5N1)). This amino acid sequence is reproduced below, with sites identified as (1) through (3) in the paragraph above underlined for clarity:

(SEQ ID NO: 1)

1 mekivllfai vslvks*dqic igyhannste qvdtimeknv tvthaqdile kthngklcdl 61 dgvkplilrd csvagwllgn pmcdefinvp ewsyivekan pvndlcypgd fndyeelkhl 121 lsrinhfeki qiipkgswps heaslgvssa cpyqgkssff rnvvwlikk nstyptikrsy 181 nntnqedllv lwgihhpnda aeqtklyqnp ttyisvgtst lnqrlvpria trskvngqsg

-continued

```
241 rmeffwtilk pndainfesn gnfiapeyay kivkkgdsti mkseleygnc ntkcqtpmga

301 inssmpfhni hpltigecpk yvksnrlvla tglrnspqre rrkkrglfga iagfieggwq

361 gmvdgwygyh hsneqgsgya adkestqkai dgvtnkvnsi idkmntqfea vgrefnnler

421 rienlnkkme dgfldvwtyn aelivimene rtldfhdsnv knlydkvrlq lrdnakelgn

481 gcfefyhkcd necmesvrng tydypqysee aklkreeisg vklesigiyq ilsiystvas

541 slalaimvag lslwmcsngs lqcr
```

The above sequence varies from the Ha et al., reference in that the reference begins with the * in the sequence given above. The exact amino acid sequence and position of the features discussed here will vary from strain to strain. The features used in the present invention are identified in variant sequences, a glycosylation site, and the receptor specificity site, as described further in Table 2. Detailed sequence information can be obtained from the web site at flu (dot) lanl (dot) gov/, the Los Alamos National Laboratory Influenza Sequence Database (ISD), which contains all published influenza viral sequences, which sequences have been curated by domain experts to ensure high standards of accuracy and completeness. (Macken, C., Lu, H., Goodman, J., & Boykin, L., "The value of a database in surveillance and vaccine selection" in Options for the Control of Influenza IV. A. D. M. E. Osterhaus, N. Cox & A. W. Hampson (Eds.) *Amsterdam: Elsevier Science,* 2001, 103-106).

The HA binds to sialic acid-terminated glycan receptors on the host cell surface, triggering virion uptake by endocytosis. Human respiratory tract cells have predominantly alpha 2-6 linked sialic acid receptors, whereas duck intestine has predominantly alpha 2-3 linked sialic acid receptors. Host-adapted human and avian influenza viruses selectively bind to homologous variant sialoside structures (Paulson 1985; Connor et al., 1994; Matrosovich et al., 2000). The HA receptor binding site is located at the convergence of one helix, two loops and three single residues near the top of the molecule; amino acid residues in the 184-186 helix as well as the 130-134 and 217-224 loops make up the rims, whereas residues 91, 149 and 179 form the floor of the cavity (H5 numbering; references: (Ha et al., 2002; Stevens et al., 2006a)). In the H3 subtype of HA, amino acids 222 and 224 are major determinants of human or avian host specificity of the virus (Vines et al., 1998). Similar changes have been documented for the H1 HA that caused the 1918 so-called Spanish influenza pandemic (Reid et al., 1999; Stevens et al., 2006b).

The HA is also responsible for cell entry by mediating fusion of the endosomal and viral membranes. The HA requires proteolytic cleavage to become functional in membrane fusion. Cleavage, mediated by host proteases, results in two disulfide-linked subunits, HA1 and HA2. The HA1 region of the HA gene encompasses three sites of known biological significance, which are targets for nucleic acid identification in the present methods:

A glycosylation sequon at amino acids 154-156 (of mature H5 HA1) has been linked to viral adaptation to chickens; the majority of H5N1 viruses isolated from humans since 2004 have this motif (Banks and Plowright 2003; WHO 2005).

The receptor-binding site. Changes in the rims or floor of the receptor-binding site thought to favor binding of human forms of cell surface sialosides are considered critical for sustained transmission in the human population.

Finally, the number of basic amino acids (lysine or arginine) in the cleavage site between HA1 and HA2 determines whether the virus is highly pathogenic for birds (Bosch et al., 1981; Ohuchi et al., 1989). All Eurasian H5N1 viruses currently circulating are highly pathogenic and contain either five or six consecutive basic amino acids at this site (WHO 2005).

Recent phylogenetic analysis of H5N1 evolution indicates that distinct major and minor clades have emerged among HA gene lineages; the two most important ones of these from a public health perspective are termed clades 1 and 2. These two clades are identifiable with two amino acids 124 and 212 (WHO 2005). These clade distinctions may be antigenically significant; therefore clade identification may aid selection of appropriate vaccines, and are also contemplated by the present methods. Rapid H5N1 identification will assist in pinpointing the source of particularly virulent outbreaks, and in targeting limited supplies of vaccines and anti-virals to key regions. Clade determinations of the samples used in the present work are shown in FIG. 1.

BRIEF SUMMARY OF THE INVENTION

The following brief summary is not intended to include all features and aspects of the present invention, nor does it imply that the invention must include all features and aspects discussed in this summary.

The present invention provides an assay for detecting the presence of H5N1 influenza virus and, furthermore, determining selected subsequences of the H5N1 hemagglutinin (HA) gene that have biological significance. Provided here are probes and primers directed to specific regions of the HA gene, namely (1) a glycosylation sequon; (The H5 and H9 HAs share three asparagine-linked glycosylation sites (at HA1 21 and 289, and HA2 154—Ha et al.) (2) the receptor binding site; and (3) the cleavage site between HA1 and HA2 (HA1/HA2 cleavage site). By focusing on these regions, small amounts of sequence information (5-30 bases) from a region identified here can yield sufficient data to classify a sample.

Other specific regions may also be targeted. In the present work, ten specific sequencing primers were used to determine HA clade and strain, receptor binding preference, etc.

In the present methods, a sample suspected of containing an influenza A virus is concentrated for virus, and any RNA is extracted and amplified by RT-PCR, whereby a DNA sequence complementary to the RNA encoding the HA gene, or a substantial portion of the HA gene is obtained. The primers chosen for this amplification are chosen to amplify any chosen influenza strain, e.g., any influenza A HA gene, or any H5N1 HA gene. For example, the first primer sequence given below for the Vietnam HN 304/08/05 returns approximately 100 hits when queried in NCI BLAST, all of which are H5N1.

Thus, the amplified sample will contain at least a significant fraction of the HA gene, e.g., about 70-100%. The amplified HA sequence is then contacted with site specific primers, e.g., primers which hybridize to regions flanking a clade marker, a strain marker, a glycosylation sequon, a receptor binding site, a cleavage site, etc. Thus, as shown in FIGS. 3-8 and Table 1 below, various internal primers, forward and reverse, are used to flank regions of interest, and subsequent PCR reactions are carried out.

Next, the sample amplified from the site specific markers is hybridized to a number of capture probes, which are complementary to a PCR primer region, preferably the 3' primer region shown, e.g., double underlined at the 3' most end of FIG. 5. The immobilized sample is then contacted with site specific (internal) primers, such as are shown underlined, which flank regions of interest, and nucleotides are dispensed for sequencing by pyrosequencing, BRC (bioluminescence regenerative cycle, as described in US PGPUB 20030082583), or the like. The primers are chosen to be generic to different strains, so that the specific identity of a given sample will be revealed by the sequence information of the chosen regions. A "consensus pre-programmed sequencing strategy" is used in the order of dispensation of nucleotides in the sequencing reaction. This reduces the need for addition of non-complementary nucleotides.

Different pyrophosphate based detection systems, in addition to pyrosequencing or BRC, may be used for DNA sequencing (e.g., Nyren and Lundin, *Anal. Biochem.* 151: 504-509, 1985; U.S. Pat. Nos. 4,971,903; 6,210,891; 6,258,568; 6,274,320).

In one aspect of the invention, the amplified sample is generated with biotinylated primers, yielding biotinylated PCR products, which may then be immobilized by binding the amplified product to streptavidin, e.g., streptavidin-coated beads.

BRIEF DESCRIPTION OF THE DRAWINGS

FIG. 3, panels A-I, show pyrograms obtained by pyrosequencing of sample A8 (A/Vietnam/HN30408/2005, aka VHN3040805) with the HS 96 system. Peaks above a given nucleotide sample indicate nucleotide incorporation (with height proportional to number of consecutive incorporation events). Initial pyrosequencing was performed with systematic nucleotide dispensation for de novo sequencing (pre-programmed dispensation runs can also be performed). A map of the HA sequence of sample A8 comparing pyrogram to Sanger sequence data is given in FIG. 6. Reverse-primed pyrosequencing results should be read as reverse complements. In FIG. 3, A is SEQ ID NO: 2; B is SEQ ID NO: 3; C is SEQ ID NO: 4; D is SEQ ID NO: 5; E is SEQ ID NO: 6; F is SEQ ID NO: 7; G is SEQ ID NO: 8; H is SEQ ID NO: 9; I is SEQ ID NO: 10.

FIG. 4 is a detail of a representative program. Pyrosequencing results obtained using the de novo (top) and consensus pre-programmed (bottom) sequencing methods for site 3 (a clade marker) in sample A1 (goose/Guangdong/1/96) are compared. Both methods give the sequence GACAAAGCTCTATCAAAAC (SEQ ID NO: 11) for our laboratory stock. In contrast the GenBank sequence (accession #AF144305) reads GACAAAGCTATATCAAAAC SEQ ID NO: 12); this difference is attributed to quasispecies variation arising from laboratory propagation. A longer read length is obtained via the consensus pre-programmed dispensation method. Note that the "de novo" method simply repeats "A-C-G-T," as can be seen in the figure, while the preprogrammed method uses a sequence that uses only bases known to be found in various subspecies of the short sequence (2-30 bases) in question.

FIG. 5 is a multiple sequence alignment carried out with the HA cDNA sequences of the 9 different samples used. For purposes of illustration, VHN3040805 is identified and numbered in consecutive groups. The underlined sequences are coded and set off by periods, and the pyrogram sequences represented in FIGS. 3,4 and 6-8 are from the sequences in FIG. 5. The code is as follows, with reference to line numbers 1-13 and the second sample, VHN3040805:

Figure 1:
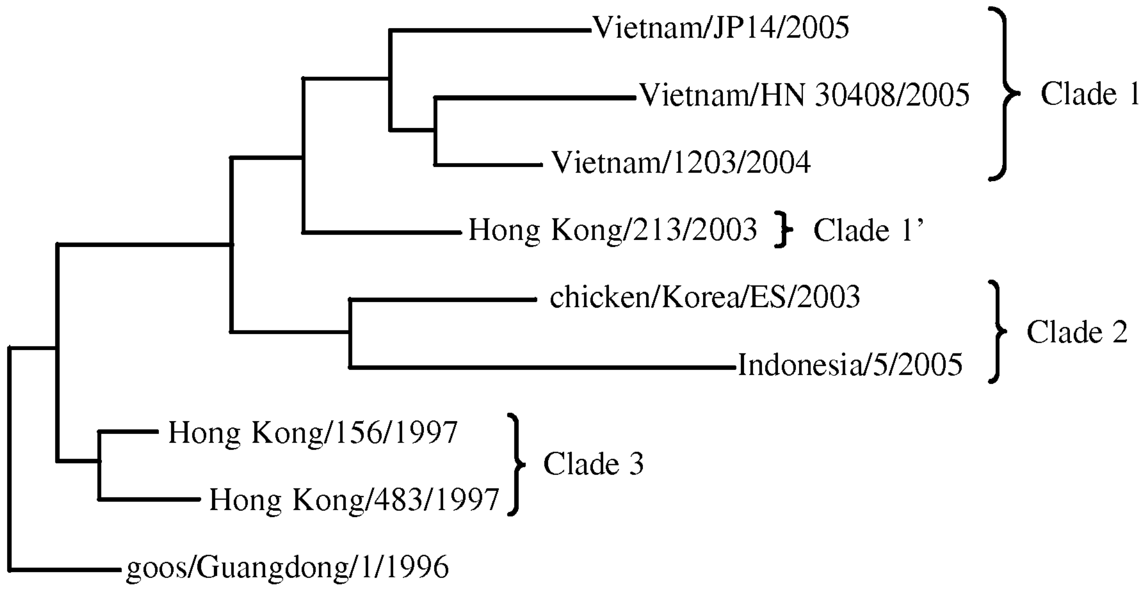
FIG. 1 is a dendrogram showing phylogenetic relationships of H5N1 hemagglutinin (HA) genes from highly pathogenic H5N1 avian influenza viruses used in this study. Phylogenetic trees were inferred from nucleotide sequences by the neighbor joining method in the MEGA program, available at http (dot)//vivo(dot)cornell(dot)edu. Horizontal distances are proportional to the number of nucleotide changes between the viruses. HA clade determinations are shown on the right.

Line 1, bold double underlining: H5N1 general primer;

Line 2, small letters: clade marker; bold underline, internal primer, reverse; underline (ll. 2-3: internal primer forward;

Line 3, double underlining: strain marker; single underline (ll. 3-4), internal primer forward; bold, lines 3-4: glycosylation sequon;

Line 5, single underline: internal primer, forward; double underline: strain marker;

Line 6, underline, internal primer, forward; small letters, clade marker; bold underline (ll. 6-7), internal primer, reverse;

Line 7, bold italics: receptor-binding site; bold underline internal primer, reverse;

Line 10, underline, internal primer, forward; double underline, strain marker;

Line 12, underline: internal primer, forward; underline italics: HA1/HA2 cleavage site; bold underline (lines 12-13): internal primer, reverse;

Line 13, double underline: H5N1 general primer.

FIG. 5 contains the following H5N1 HA sequences: (1) VN120304 (SEQ ID NO: 13); (2) VHN3040805 ((SEQ ID NO: 14); (3) VNJP1405 (SEQ ID NO: 15); (4) HK21303 (SEQ ID NO: 16); (5) CkKoreaES03 (SEQ ID NO: 17); (6) Indonesia505 (SEQ ID NO: 18); (7) GsGuangdong 196 (SEQ ID NO: 19); (8) HK15697 (SEQ ID NO: 20); (9) HK 48397 (SEQ ID NO: 21).

FIG. 6A-H is a pyrogram showing results from Sample A8, Vietnam/HN30408/05, the 2nd sequence in FIG. 5; each pyrogram shows sequencing results from a different region of the sample;

FIG. 7 A-H is a pyrogram showing results from Sample A9, Duck/Kulon Progo/BBTEV/9/04; each pyrogram shows sequencing results from a different region of the sample.

FIG. 8A-H is a pyrogram showing results from Sample A10, Indonesia 5/05, the $6^{th}$ sequence in FIG. 5; each pyrogram shows sequencing results from a different region of the sample.

DETAILED DESCRIPTION OF THE PREFERRED EMBODIMENT

Overview

Described below is a method for identifying strains of an influenza virus, in particular H5N1, which in a preferred embodiment uses pyrosequencing technology to obtain characteristic short sequences of the virus. The method targets the hemagglutinin (HA) gene of H5N1 influenza. The assay uses RT-PCR to amplify a known H5N1-specific region of 768 nucleotides. Subsequent pyrosequencing (Ronaghi et al., 1998) of strains that are H5N1-positive with ten specific sequencing primers is used to determine HA clade and strain, receptor binding preference, low or high pathogenicity cleavage site and glycosylation status. The assay presented here is considerably more informative than traditional techniques, as it not only identifies the H5N1 lineage but also predicts receptor-binding properties that could herald the development of human-human transmissibility. Moreover, this assay is specific, rapid and cost-effective. Because specific regions of biological significance and differentiation are identified, only short sequence lengths are needed.

Representative strains are presented and the analysis of the HA gene region is described. FIG. 5 shows a multiple sequence alignment of the exemplary strains, with the particular primers and markers used indicated. By presenting these data in a sequence alignment format, it can be seen that the various representative sample sequences are identical for primer regions, yet different for regions of discrimination as found here. Primers, markers and key sites on H5N1 influenza A hemagglutinin gene are thus identified. That is, any HA gene sequence will hybridize to the primer. Strain determination is made by obtaining sequences adjacent the primers. A region of 768 bases of cDNA for hemagglutinin gene of nine strains of H5N1 was assayed to obtain sequence information for three key biologically significant sites (glycosylation, receptor specificity, and HA1/HA2 cleavage. Two clade markers were also used to distinguish clades of H5N1 (FIG. 5, lines 2 and 6 small bold "ag"). Three additional polymorphic sites (line 3 double underline, line 5 double underline, line 10 double underline) provide unambiguous strain identification. The PCR primers used to bracket this entire region are shown at the 5' and 3' ends in connection with FIG. 5.

DEFINITIONS

All terms are used herein in their scientifically accepted sense, and are intended to be made more definite by the definitions below.

The term "glycosylation sequon" means the sequence where an oligosaccharide chain is attached to a protein by oligosaccharyl transferase, namely an asparagine occurring in the tripeptide sequence Asn-X-Ser or Asn-X-Thr, where X could be any amino acid except Pro.

The term "receptor binding site" means the portion of the HA gene which mediates binding of the influenza virus to host cells. The cellular receptors that HAs recognize are sialic acids linked to cell-surface glycoproteins and glycolipids. All subtypes of HA found in avian species prefer binding to sialic acid in a 2,3-linkage to galactose. In contrast, the HAs of human viruses recognize sialic acid in 2,6-linkage. As a consequence, the cross-species transfer of avian viruses into humans that results in pandemics requires a change in binding specificity. The mechanism that human viruses have used to achieve these changes appears to be different for different subtypes. For the HAs of the H2 and H3 human viruses a minimum of two changes in binding site amino acids, Gln-226->Leu and Gly-228->Ser, are thought to correlate with the shift from binding avian to binding human receptors. In contrast, HAs of human H1 viruses (including the 1918 virus) acquire binding to human receptors while retaining Gln-226 and Gly-228. (See, Science 303, 1838-1842 (2004); www (dot)esrf(dot)fr/UsersAndScience/Publications/Highlights/2004/SB/SB4/).

The term "HA1/HA2 cleavage site" means the site where, for full infectivity, the single chain (HA0) is cut into two chains (HA1 and HA2). This site is illustrated at www-ssrl (dot)slac(dot)stanford(dot)edu/research/highlights archive/1918flu(dot)html. The term is further explained in Zhirnov et al., "Cleavage of Influenza A Virus Hemagglutinin in Human Respiratory Epithelium Is Cell Associated and Sensitive to Exogenous Antiproteases," *J Virol.* 2002 September; 76(17): 8682-8689. As explained there, the major characteristic of the HA that determines sensitivity to host proteases is the composition of the proteolytic site in the external loop in the HA0 molecule which links HA1 and HA2. This loop may contain either a single Arg or Lys residue (monobasic cleavage site) or several Lys and/or Arg residues, with an R-X-K/R-R motif, which form a multibasic cleavage site. The multibasic cleavage site of HA exists in influenza A virus subtypes H5 and H7. All other influenza A viruses and influenza B and C viruses contain HAs with a monobasic cleavage site.

The term "RT-PCR" means the reverse transcription polymerase chain reaction, a technique for amplifying a defined piece of a ribonucleic acid (RNA) molecule. The RNA strand is first reverse transcribed into its DNA complement or complementary DNA, followed by amplification of the resulting cDNA using polymerase chain reaction. Kits for carrying out this process are commercially available, such as the Titan one-tube reverse transcriptase PCR [RT-PCR] kit (Roche). Exemplary protocols may be found, e.g., in U.S. Pat. No. 6,015,664 to Henrickson, et al., issued Jan. 18, 2000, entitled "Multiplex PCR assay using unequal primer concentrations to detect HPIV 1, 2, 3 and RSV A,B and influenza virus A, B."

The term "pyrosequencing" means sequencing in which DNA samples are contacted with primers to determine the starting point of complementary strand synthesis, and further contacted with DNA synthesizing enzymes, an enzyme apyrase to decompose dNTP (deoxynucleotide triphosphates) which has been added as a substrate and remained unreacted; sulfurylase to convert pyrophosphate into ATP; luciferin; and luciferase involved in the reaction of luciferin with ATP. These reagents are placed in a titer plate. At this moment, no complementary strand synthesis occurs because dideoxynucleotides (ddNTPs), a substrate for the reaction, is not present. Four kinds of ddNTPs (i.e., dATP, dCTP, dTTP and dGTP) are added in a designated order by an ink jet system. If dCTP is the designated base to be synthesized, no reaction occurs when dATP, dTTP or dGTP is added. Reaction occurs only when dCTP is added, then the complementary strand is extended by one base length, and pyrophosphate (PPi) is released. This pyrophosphate is converted into ATP by ATP sulfurylase and the ATP reacts with luciferin in the presence of luciferase to emit chemiluminescence. This chemiluminescence is detected using a secondary photon multiplier tube or the like. Remaining dCTP or unreacted dNTP is decomposed by apyrase, which converts it into a form that has no effect on the subsequent repetitive dNTP injection and the reaction that follows. The four kinds of dNTP are added repeatedly in a designated order and the base sequence is determined one by one according to the presence or absence of chemiluminescence emitted each time (see Ronaghi, M. et al., *Science* 281, 363-365 (1998) and U.S. Pat. No. 6,841,128 to Kambara, et al., issued Jan. 11, 2005, entitled "DNA base sequencing system").

The term "bioluminescence regenerative cycle" means a process in which steady state levels of bioluminescence result from processes that produce pyrophosphate. Pyrophosphate reacts with adenosine 5'-phosphosulphate in the presence of ATP sulfurylase to produce ATP. The ATP reacts with luciferin in a luciferase-catalyzed reaction, producing light and regenerating pyrophosphate. The pyrophosphate is recycled to produce ATP and the regenerative cycle continues. This process is described in detail in US 2003/0082583 to Hassibi, et al., published May 1, 2003, entitled "Bioluminescence regenerative cycle (BRC) for nucleic acid quantification."

The term "identical" when used in terms of sequence identity means that two polypeptide or nucleic acid sequences are identical (i.e., on a residue-by-residue basis) over the window of comparison. The term "percentage of sequence identity" is calculated by comparing two optimally aligned sequences over the window of comparison, determining the number of positions at which the identical residue occurs in both sequences to yield the number of matched positions, dividing the number of matched positions by the total number of positions in the window of comparison (i.e., the window size), and multiplying the result by 100 to yield the percentage of sequence identity. For sequences less than about 50 residues, the comparison window will be the entire length of the sequence. It is preferred here, that nucleic acid sequences of less than about 50 residues, preferably less than about 30 residues, as exemplified in Table 1, will be considered. For example, in a sequence of 20 residues, 90% identity would mean 18 of 20 residues are identical, with standard (no penalty) gapping allowed.

Methods and Materials

Avian Influenza A Subtypes and H5N1-Specific Primer Design

Sequences of 362 avian influenza A virus species were acquired from GenBank at the National Center for Biotechnology Information and Influenza Sequence Database at Los Alamos National Laboratory and aligned using Clustal X version 1.83 (Thompson et al., 1997). A specific sequencing primer was designed for H5N1, with no sequence similarity to the other influenza virus HA subtypes based on the database searches and alignments (5' and 3' ends in FIG. 5, lines 1 and 13 double underlining).

H5N1 Avian Influenza Virus Isolates

The viruses that formed the test set for this study were chosen on the basis of their diversity in biologically significant regions of hemagglutinin and/or their ability to cause infection in humans. Virus strain names are shown in FIG. 5 and accession numbers are as follows: A/goose/Guangdong/1/96 (AF144305), A/Hong Kong/156/97 (AF036356), A/Hong Kong/483/97 (AF046097), A/Hong Kong/213/2003 (AY575869), A/chicken/Korea/ES/03 (AY676035), A/Vietnam/1203/2004 (AY651334), A/Vietnam/JP14/2005 (ISDN117778), A/Vietnam/HN30408/2005 (ISDN119678), A/Indonesia/5/05 (ISDN125873).

RNA Extraction, RT-PCR and PCR Amplification

Viral RNA was extracted using the QIAmp vRNA Kit (Qiagen, Valencia Calif.). Extractions were performed according to manufacturer's instructions. QIAGEN Onestep RT-PCR kit (Qiagen, Valencia Calif.) was used to perform RT-PCR from 3 PI of RNA in a 50 PI reaction volume. The RT-PCR amplification primers, which are biotinylated F-H5N1-1/3 (5'-TCAATGACTATGAAGAATTGAAACA-3'), (SEQ ID NO: 22) and R-H5N1-2/4 (5'-AACCATCTACCATTCCCTGCCATCC-3) (SEQ ID NO: 23) were synthesized by IDT (Coralville, Iowa, USA). RT-PCR was performed with a DNA Engine (PTC-200) Peltier Thermal Cycler (BIO-RAD, Hercules, Calif.) as follows: 50° C. for 10 minutes, 95° C. for 15 minutes, 35 cycles of 95° C., 55° C., and 72° C. for 1 minute each, and finally a 10 minute final extension at 72° C. To confirm proper amplification, PCR products were electrophoresed in a 1% agarose gel and visualized by ethidium bromide staining under UV illumination. (Note: Y=C or T).

Sanger Dideoxy DNA Sequencing of PCR Products

The amplified DNA from all isolates was cycle sequenced in both directions using the BigDye Terminators Reaction Kit v. 3.1 (Applied Biosystems, Foster City, Calif.) on an ABI automated DNA sequencer (3730 XL DNA Analyzer).

Hemagglutinin Sequencing Primers

An entropy-based analysis of genetic variation among H5N1 strains (shown by multiple sequence alignment in FIG. 5) was used to design PCR primers (Cover and Thomas 1991). The approach focused on amplicons comprising regions for receptor binding sites, cleavage site and glycosylation sites, along with markers to identify clade and individual strain. Highly conserved sites were selected as internal sequencing primers to sequence each region of interest. The selected region is bracketed by sequences unique to and highly conserved in the H5N1 subtype. Based on sequence alignments of H5N1 and sequencing results (data not shown) from all the isolates, a set of sequencing primers were designed spanning a region of the HA informative with regards to clade, strain, receptor binding motif, cleavability and glycosylation sites and which specifically hybridize to H5N1. Sequences for relevant influenza viruses with known properties and virulence status were compiled for each sample from pyrograms. These sequences were then compared to known H5N1 sequences by alignment and visual inspection. The correct sequence obtained by the present primers was checked by pyrosequencing. FIG. 3 illustrates the pyrosequencing results. The strain marker having double underline in block 3 of FIG. 5 was confirmed, for example, to be SEQ ID NO: 2. SEQ ID NO: 3 was confirmed as corresponding to sequence beginning at line 4, FIG. 5. SEQ ID NO: 4 was confirmed as corresponding to sequence in the region of the double underline strain marker in block 5 of FIG. 5. Other sequences were similarly confirmed.

Pyrosequencing

Biotinylated PCR product (10 μl) from RT step from viral RNA (strain sequences shown in FIG. 5) was immobilized onto 2.5 μl streptavidin-coated High Performance Sepharose beads (Amersham Biosciences, Piscataway, N.J.) by incubation at room temperature for at least 10 minutes with agitation at 1400 rpm. Single-stranded DNA was obtained by washing the immobilized PCR product with 70% EtOH, denatured with 0.2 M NaOH, and washed with TE-Buffer (0.1 M Tris-Acetate, pH 7.6) using a Vacuum Prep Tool and Vacuum Prep Worktable (Biotage, Uppsala, Sweden). The beads were then suspended in 12 μl annealing buffer (10 mM Tris-acetate pH 7.75, 5 mM Mg-acetate) containing 0.3 pmol sequencing primer. Single-stranded DNA was hybridized to the sequencing primer by incubation at 90° C. for 2 minutes, at 60° C. for 5 minutes and at room temperature for 5 minutes.

Primed single-stranded PCR products were sequenced using PSQ™ HS96A System (Biotage). Sequencing was performed in a total volume of 12 PI using the PSQ 96 Gold kit (Biotage). Pyrosequencing was performed with consensus pre-programmed dispensation orders which were determined by integrating sequence information for each strain at a given sequencing site (Gharizadeh et al., 2005). Negative-control nucleotide dispensations were also included in these backgrounds to check for insertions and to measure background signals. The identity and number of nucleotide extension events were determined by automated measurement of the amount of light generated after incorporation of each dNTP.

Raw data were interpreted using software developed specifically for this purpose, "Classifier." Classification of samples by strain is straightforward using the short sequence segments obtained. That is, the various short sequence segments uniquely identify a specific strain. The longest sequence needed is about 22-30 bases long. The strain markers, glycosylation site and clade markers as identified in connecting with FIG. 5 all provide sequence information which when combined uniquely identify one strain. We used a Support Vector Machine (Cristianini and Shawe-Taylor 2000) approach implemented in the statistical programming language R (R Statistical Package) to classify a given sample with statistical accuracy. This provides an automated sample identification tool, designed for eventual use with large numbers of source sequences (Duda et al., 2001; Meyer 2006). As can be seen from FIG. 5, one may visually inspect the different sequences obtained for the two clade markers, the three strain markers, the glycosylation site, the receptor specificity site, and the cleavage site and identify a particular isolate. Additional isolates may be added to the present data, and sequence searches run using a variety of known algorithms.

Results

HA Amplification by PCR

Figure 2:
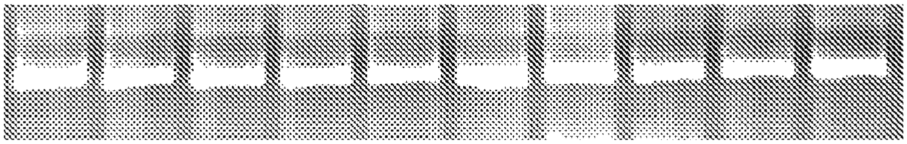
FIG. 2 is a Southern blot of amplicon DNA yield from PCR with different combinations of biotinylated primers. From left to right, samples A1-A9, with a biotinylated forward primer (B-F-H5N1-1) and nonbiotinylated reverse primer (R-H5N1-2).

The first step in the analysis of a clinical specimen or a viral isolate in our assay is the generation of a DNA copy of the viral RNA, which is accomplished by reverse transcription coupled to PCR (RT-PCR). This was accomplished using two different biotinylated combinations of PCR primers specific to the H5N1 regions of interest in order to achieve optimal sequencing flexibility of H5N1 isolates, as listed in FIG. 1. As shown in FIG. 2, either pair of primers provided reliable amplification of H5N1, and neither generated products when used in PCRs with negative controls (total genomic DNA from unrelated human cell lines).

All of the H5N1 PCR products were sequenced at least twice both by Sanger dideoxy sequencing and pyrosequencing; PCR-positive amplicons generated correct sequence results independent of sequencing method or fragment size. Furthermore, no loops or primer-dimers were observed when primers were pyrosequenced in the absence of template. A representative and typical pyrogram of Sample A8 (A/Vietnam/HN30408/2005) obtained by pyrosequencing is shown in FIG. 4 and FIG. 6; pyrograms for additional samples are in FIGS. 7-8. Supplemental sequence information is in the provisional patent application. The pyrosequencing run covering the required 14 bases took approximately 15 minutes.

HA Pyrosequencing

The results of our pyrosequencing assay clearly distinguished the nine different strains of H5N1 avian influenza, based on eight sites, as shown in Table 1. Table 1 shows sequences of H5N1 clade markers and active sites, as determined by pyrosequencing. Sample strains are listed in the leftmost column, abbreviated sequencing primer name in the top row. "F" or "R" indicates whether the primer is forward- or reverse-directed. The 5'-3' sequences presented here were obtained by reading pyrograms (as reverse complements when using a reverse-directed sequencing primer).

TABLE 1

Part A

| | Clade Marker 1 | Strain Marker 1 | Glycosylation Site | Strain Marker 2 | Clade Marker 2 (F) |
|---|---|---|---|---|---|
| Goose/Guangdong/1/96 | AACCTGGTTCTTGAAACCCATCA SEQ ID NO: 25 | ATGGGAGGTCCTCCTTTTTTCAGAAA SEQ ID NO: 32 | GTGCATACCCAACAATAAA SEQ ID NO: 40 | GACAAAGCTCTA SEQ ID NO: 47 | TACCAGAAATAGCTACTAGACCAA SEQ ID NO: 50 |
| Hong Kong/156/97 | AACCTGGTTCTTGAAACCCATCA SEQ ID NO: 25 | TTGGGAGGTCCTCCTTTTTCAGA SEQ ID NO: 33 | GTACATACCCAACAATAAAGA SEQ ID NO: 41 | GACAAAGCTCTA SEQ ID NO: 47 | TACCAGAAATAGCTACTAGACCAA SEQ ID NO: 50 |
| Hong Kong/483/97 | AACCTGGTTCTTGAAACCCATCA SEQ ID NO: 25 | TTGGGAAGTCCTCCTTTTTCAGA SEQ ID NO: 34 | GTACATACCCAACAATAAAGA SEQ ID NO: 41 | GACAAAGCTCTA SEQ ID NO: 47 | TCCAGAAATAG SEQ ID NO: 51 |
| Hong Kong/213/03 | GACCTGGTTCTTAAACCCATCA SEQ ID NO: 26 | AAGGAAAGTCCTCCTTTTTCAG SEQ ID NO: 35 | ATGCATACCCAACAATAA SEQ ID NO: 42 | GACAAAGCTCTA SEQ ID NO: 47 | TCCAGAAATAG SEQ ID NO: 51 |
| Chicken/Korea/ES/03 | AGCCTGGTTCTTGAAACCCATCA SEQ ID NO: 27 | AGGGAAGGTCCTCCTTCTTCAGAAA SEQ ID NO: 36 | GTGCACTACCCAACAATAAA SEQ ID NO: 43 | GACAAGACTCTA SEQ ID NO: 48 | ACCAAAAA SEQ ID NO: 52 |
| Vietnam/1203/04 | GACCTGGTTCTTGAAACCCATCA SEQ ID NO: 28 | AGGGAAAAGTCCTCCTTTTTCAGA SEQ ID NO: 37 | GTACATACCCAACAATAAAGA SEQ ID NO: 41 | GACAAAGCTCTA SEQ ID NO: 47 | ACCAAAGAA SEQ ID NO: 53 |
| Vietnam/JP14/05 | GACCTCGGTCTT SEQ ID NO: 29 | AGGGAAAGTCCTCCTTTTTCAGAAA SEQ ID NO: 38 | GTACATACCAACAATAAAGAAA SEQ ID NO: 44 | GACAAAGCTCTA SEQ ID NO: 47 | ACCAAGAA SEQ ID NO: 54 |

TABLE 1-continued

| | | | | | |
|---|---|---|---|---|---|
| Vietnam/<br>HN304/<br>08/05 | CAGCCTGGTTCTT<br>GAAACCCATCA<br>SEQ ID NO: 30 | AGGGAAAGTCCTC<br>CTTTTTCAGAAA<br>SEQ ID NO: 38 | GTACATACCCA<br>ACAATAAGA<br>SEQ ID NO: 45 | GACAAAGCT<br>CTA<br>SEQ ID NO: 47 | ACCGAAGAA<br>SEQ ID NO: 55 |
| Indonesia/<br>5/05 | CAGCCTGGTTCTT<br>GAAAGGGATCA<br>SEQ ID NO: 31 | TGGGAAGTCCCTC<br>CTTTTTTAGA<br>SEQ ID NO: 39 | GTACATACCCA<br>ACAATAAAGAA<br>SEQ ID NO: 46 | GACAAGGCT<br>ATA<br>SEQ ID NO: 49 | ACCAAAGAA<br>SEQ ID NO: 53 |

Part B

| | Clade Marker 2 (R) | Receptor Specificity Site | Strain Marker 3 | Cleavage Site |
|---|---|---|---|---|
| Goose/<br>Guangdong/<br>1/96 | AGACCTTGGTT<br>SEQ ID NO: 56 | GTAAGAAGGTGAAACGG<br>GCAAATGAAACCCAGA<br>SEQ ID NO: 64 | CTCTAGTATGCCA<br>SEQ ID NO: 73 | AGAAGAAGAAAA<br>AAGAGAGAGGA<br>SEQ ID NO: 78 |
| Hong Kong/<br>156/97 | AGACCTTGGTTAG<br>AGA<br>SEQ ID NO: 57 | GTAAGAAGGTGGAAACG<br>GGCAAATG<br>SEQ ID NO: 65 | CTCTAGTATGCCA<br>SEQ ID NO: 73 | AGAAGAAGAAAA<br>AAGAGA<br>SEQ ID NO: 79 |
| Hong Kong/<br>483/97 | AGACCTTTGGTT<br>SEQ ID NO: 58 | ATAAGAAGGTGAAACGG<br>GC<br>SEQ ID NO: 66 | CTCTAGTATGCCA<br>SEQ ID NO: 73 | AGAAGAAGAAAA<br>AAGAGA<br>SEQ ID NO: 79 |
| Hong Kong/<br>213/03 | AAACCATGGTTAG<br>AGACCAAATCACA<br>SEQ ID NO: 59 | GTAGGAAGGTAAAAC<br>SEQ ID NO: 67 | CTCTAGTATGCCA<br>SEQ ID NO: 73 | AGAAGAAGAAAA<br>AAGAGAGGA<br>SEQ ID NO: 80 |
| Chicken/<br>Korea/<br>ES/03 | AAACCATGGTTAG<br>AGACAA<br>SEQ ID NO: 60 | GTAGGAAGGTGAAACGG<br>GCA<br>SEQ ID NO: 68 | CTCTAGTA<br>SEQ ID NO: 74 | AAAAGAAAAAAG<br>AGA<br>SEQ ID NO: 81 |
| Vietnam/<br>1203/04 | Unreadable | GTAGGAAGGTGAAACGG<br>GGC<br>SEQ ID NO: 69 | CTCTAGCATGCCA<br>SEQ ID NO: 75 | Unreliable |
| Vietnam/<br>JP14/05 | GAAACCCATGG<br>SEQ ID NO: 61 | GTAGGAGGGTGAAACGG<br>GC<br>SEQ ID NO: 70 | CTCTAGTATGCCAC<br>SEQ ID NO: 76 | AGAAGAAGAAAA<br>AAGAGA<br>SEQ ID NO: 79 |
| Vietnam/<br>HN304/<br>08/05 | GAAACCCATGGTT<br>AGAGACCAAAT<br>SEQ ID NO: 62 | GTAGGAAGGTG<br>SEQ ID NO: 71 | TTCTAGTATGCCA<br>SEQ ID NO: 77 | AGAAGAAAAAAG<br>AGAGG<br>SEQ ID NO: 82 |
| Indonesia/<br>5/05 | AAACC<br>SEQ ID NO: 63 | GTAGGAAGGTGAAACGG<br>GC<br>SEQ ID NO: 72 | CTCTAGTATGCCA<br>SEQ ID NO: 73 | AGCAGAAGAAAA<br>AAGAGA<br>SEQ ID NO: 83 |

Using Vietnam/120304 as an example, the marker sequences may be correlated to the full sequence given in FIG. 5, first line. "Strain Marker 1" corresponds to double underlining in block 3. "Gycosylation site" begins with the underlined portion in line 4, but extends further. "Strain Marker 2" corresponds to the single underlined part of Block 5. Clade Marker 2(F) is bolded for that sample, for purposes of illustration. The reverse, of course, would be the reverse complement, which may also be used for any of the sequences in question. Strain marker 3" of the Table as listed stops about one base short of the underlined portion at FIG. 5, block 10. The cleavage site of the Table contains an extra two bases beyond those underlined in FIG. 5, block 12. Therefore, it can be seen that there is some flexibility surrounding the exact sequences to be used. Enough sequence information should be included so that the markers used, when complied for a given sample unambiguously identify the sample as to strain, at the least, and may in addition provide additional biological information. Furthermore, this approach provided accurate sequencing of regions of known biological significance. The results of this assay can be seen in Table 2, which shows the amino acid sequences characteristic of each strain tested.

lates in amino acids 221-224 of the HA1, is GQSG (SEQ ID NO: 84). One human isolate, sample A4 (Hong Kong/213/03) had a mutation at amino acid 223, S>N, which switches the affinity of the hemagglutinin from alpha 2-3 linked sialic acid too the alpha 2-6 linked sialic acid preferred by the human influenza virus. This mutation was detected by a single nucleotide change G>A, in the sequence of the receptor binding active site. Rapid characterization of the receptor binding active site and other active sites of the hemagglutinin is critical in identification of viruses with increased pandemic potential. In addition, one may use the present methods to discern the identity of the strain quite readily.

Strain markers (three short regions) were selected based on entropy-based analysis of variation across the nine H5N1 strains used for testing (Cover and Thomas 1991).

The results described here indicate that targeted pyrosequencing approach can clearly distinguish among different strains of H5N1, and can accurately sequence regions of known biological significance. The HA sequence results obtained by pyrosequencing were 100% identical to those obtained by the Sanger method (two replicates were performed in order to obtain the longest possible read-lengths

TABLE 2

Characterization of the hemagglutinin from the H5N1 influenza viruses used in this study.

| Virus Name | HA clade | Glycolation Motif (NXT/S, X ≠ P) at aa 154 | Receptor Binding Site (221-224) | Cleavage Motif | Host/Outcome |
|---|---|---|---|---|---|
| Goose/ Guangdong/ 1/96 | ancestor | Present | GQSG SEQ ID NO: 84) | RRRKKR (SEQ ID NO: 86) | Goose |
| Hong Kong/ 156/97 | 3 | Absent | GQSG SEQ ID NO: 84) | RRRKKR (SEQ ID NO: 86) | Human/Died |
| Hong Kong/ 483/97 | 3 | Present | GQSG SEQ ID NO: 84) | RRRKKR (SEQ ID NO: 86) | Human/Died |
| Hong Kong/ 213/03 | 1' | Present | GQNG SEQ ID NO: 85) | RRRKKR (SEQ ID NO: 86) | Human/Died |
| Vietnam/ 1203/04 | 1 | Present | GQSG SEQ ID NO: 84) | RRRKKR (SEQ ID NO: 86) | Human/Died |
| Vietnam/ JP14/05 | 1 | Present | GQSG SEQ ID NO: 84) | RRRKKR (SEQ ID NO: 86) | Human/Died |
| Vietnam/ HN30408/05 | 1 | Present | GQSG SEQ ID NO: 84) | RRKKR (SEQ ID NO: 87) | Human/Survived |
| Chicken/ Korea/ ES/03 | 2 | Absent | GQSG SEQ ID NO: 84) | KRKKR (SEQ ID NO: 88) | Chicken |
| Indonesia/ 5/05 | 2 | Present | GQSG SEQ ID NO: 84) | SRRKKR (SEQ ID NO: 24) | Human/Died |

In order to characterize the strains based on the HA sequence, pyrograms obtained via pyrosequencing were visually inspected to verify the sequences of relevant active sites and the presence of polymorphisms that could serve as lineage markers. These sequences were then compared to known H5N1 sequences for clade and strain identification. Certain positions provided essential information for the identification of signatures important for public health, such as changes in the receptor-binding site, which could signal an increase in the ability of the virus to transmit from human to human. The prototypical receptor-binding site for avian isoand to cross-verify results). Three pyrosequencing replicates, with nine samples at ten sites, were performed; two with a de novo dispensation and one with a pre-programmed dispensation order. Of the three pyrosequencing replicates performed, all successful runs verified one another. Because Sanger sequencing relies on molecular separation of the polymerase-mediated extension of the primer, the first ~20-50 bases 3' of the primer are not discernible In contrast, pyrosequencing provides unambiguous sequence from the first nucleotide 3' to the primer, increasing the sequence information yield per assay. This feature of pyrosequencing was exploited by designing H5N1-specific primers adjacent to critical polymorphic sites such that the initial base-callings are usually sufficient to determine the lineage of a given HA gene. Given the sequence information presented here, one could design sequencing primers adjacent to any of the markers illustrated.

While a simpler detection assay that gives a positive or negative identification of H5N1 will be helpful, a more information-rich method, such as the one described here, may provide additional crucial information to guide patient care or public health measures aimed at preventing or controlling a pandemic. As this pathogen becomes more prevalent, it will be impractical to perform full sequencing of all isolates in time for analysis of rapidly changing epidemiological trends. Our assay could be a valuable complement to full sequencing at public health laboratories. Also, as strains emerge which are resistant to anti-virals or escape a vaccine response, it will be necessary to have a rapid strain typing method for use in determining clinical treatment. We have developed a rapid and inexpensive assay based on DNA sequencing, the gold-standard method producing the highest resolution for nucleic acid-based diagnosis, for early detection of virus present in host cells. This assay permits rapid, simplified and highly accurate identification of avian H5N1 influenza A virus, and consists of inexpensive and simple procedures maintaining high sensitivity and specificity. As new sites of functional relevance are identified, new site-specific primers can be added to broaden the utility of the assay. Expanded knowledge of H5N1 sequence and evolution will contribute to more effective diagnostic methods and treatments that require less investment of time and money.

The above results have validated our approach and selection of specific primers. We have moved toward a further refinement of the assay based on these results. After an initial de novo pyrosequencing run was performed on the H5N1 samples, sequence data for each strain were compiled for each nucleotide site. This information was integrated to produce consensus pre-programmed dispensation orders of nucleotides. This type of pyrosequencing would allow us to obtain sequence results of similarly high quality in 10 to 15 minutes (FIG. 4). With this approach, all known H5N1 subtypes could be positively identified. New variants would not be fully characterized, but would be heralded by truncated sequences.

In summary, we have developed a reliable, rapid, cost-effective, and information-rich diagnostic assay for H5N1 influenza. This sequence-based method could be extended to include amplicons from other genes of interest; for example, drug targets such as NA and the M2 ion channel (Scheffner 1998; Li et al., 2004), or the postulated virulence motifs on NS1 or PB2 (Hatta et al., 2000; Obenauer et al., 2006). Pyrosequencing is user-friendly, and permits significantly more efficient and rapid genotyping than traditional techniques. This method detects a wide range of influenza A H5N1 subtypes based on sequence information. This assay will allow further development of technology to directly detect H5N1 or specific strains of influenza A in clinical specimens without extensive sample preparation. In addition, BRC may be used for sequencing, without amplification of the viral RNA or resultant cDNA.

CONCLUSION

The above specific description is meant to exemplify and illustrate the invention and should not be seen as limiting the scope of the invention, which is defined by the literal and equivalent scope of the appended claims. Any patents or publications mentioned in this specification are indicative of levels of those skilled in the art to which the patent pertains and are intended to convey details of the invention which may not be explicitly set out but which would be understood by workers in the field. Such patents or publications are hereby incorporated by reference to the same extent as if each was specifically and individually incorporated by reference, as needed for the purpose of describing and enabling the method or material referred to.

REFERENCES 1. (CDC) (2006) "New laboratory assay for diagnostic testing of avian influenza A/H5 (Asian Lineage)." *MMWR Morb Mortal Wkly Rep* 10(55(5)): 127.
2. Banks J, Plowright L (2003) "Additional glycosylation at the receptor binding site of the hemagglutinin (HA) for H5 and H7 viruses may be an adaptation to poultry hosts, but does it influence pathogenicity?" *Avian Dis* 47(3 Suppl): 942-950.
3. Bosch F X, Garten W, Klenk H D, Rott R (1981) "Proteolytic cleavage of influenza virus hemagglutinins: primary structure of the connecting peptide between HA1 and HA2 determines proteolytic cleavability and pathogenicity of Avian influenza viruses." *Virology* 113(2): 725-735.
4. Connor R J, Kawaoka Y, Webster R G, Paulson J C (1994) "Receptor specificity in human, avian, and equine H2 and H3 influenza virus isolates." *Virology* 205(1): 17-23.
5. Cover T M, Thomas J A (1991) Elements of information theory. New York: Wiley. xxii, 542 p. p.
6. Cristianini N, Shawe-Taylor J (2000) "An introduction to support vector machines and other kernel-based learning methods." Cambridge, U.K.; New York: Cambridge University Press. xiii, 189 p.
7. Duda R O, Hart P E, Stork D G (2001) Pattern classification. New York; Chichester [England]: Wiley. xx, 654 p. p.
8. Effler P V, Ieong M C, Tom T, Nakata M (2002) "Enhancing public health surveillance for influenza virus by incorporating newly available rapid diagnostic tests." *Emerg Infect Dis* 8(1): 23-28.
9. Fan J, Henrickson K J, Savatski L L (1998) "Rapid simultaneous diagnosis of infections with respiratory syncytial viruses A and B, influenza viruses A and B, and human parainfluenza virus types 1, 2, and 3 by multiplex quantitative reverse transcription-polymerase chain reaction-enzyme hybridization assay (Hexaplex)." *Clin Infect Dis* 26(6): 1397-1402.
10. Gharizadeh B, Akhras M, Unemo M, Wretlind B, Nyren P et al., (2005) "Detection of gyrA mutations associated with ciprofloxacin resistance in Neisseria gonorrhoeae by rapid and reliable pre-programmed short DNA sequencing." *Int J Antimicrob Agents* 26(6): 486-490.
11. Ha Y, Stevens D J, Shekel J J, Wiley D C (2002) "H5 avian and H9 swine influenza virus hemagglutinin structures: possible origin of influenza subtypes." *Embo J* 21(5): 865-875.
12. Habib-Bein N F, Beckwith W H, 3rd, Mayo D, Landry M L (2003) "Comparison of SmartCycler real-time reverse transcription-PCR assay in a public health laboratory with direct immunofluorescence and cell culture assays in a medical center for detection of influenza A virus." *J Clin Microbiol* 41(8): 3597-3601.
13. Hatta M, Asano Y, Masunaga K, Ito T, Okazaki K et al., (2000) "Mapping of functional domains on the influenza A virus RNA polymerase PB2 molecule using monoclonal antibodies." *Arch Virol* 145(9): 1947-1961.

14. Li K S, Guan Y, Wang J, Smith G J D, Xu K M et al., (2004) "Genesis of a highly pathogenic and potentially pandemic H5N1 influenza virus in eastern Asia." *Nature* 430(6996): 209-213.

15. Matrosovich M, Tuzikov A, Bovin N, Gambaryan A, Klimov A et al., (2000) "Early alterations of the receptor-binding properties of H1, H2, and H3 avian influenza virus hemagglutinins after their introduction into mammals." *J Virol* 74(18): 8502-8512.

16. Meyer D (2006) Support Vector Machines. Available: http(dot)//cran(dot)r-project(dot)org/src/contrib/Descriptions/e1071(dot)html.

17. Obenauer J C, Denson J, Mehta P K, Su X P, Mukatira S et al., (2006) "Large-scale sequence analysis of avian influenza isolates." *Science* 311(5767): 1576-1580.

18. Ohuchi M, Orlich M, Ohuchi R, Simpson B E, Garten W et al., (1989) "Mutations at the cleavage site of the hemagglutinin after the pathogenicity of influenza virus A/chick/Penn/83 (H5N2)." *Virology* 168(2): 274-280.

19. Paulson J C (1985) *The Receptors*; Conn M, editor. Orlando, Fla.: Academic. 131-219 p.

20. R Statistical Package http(dot)//www(dot)r-project(dot)org/.

21. Reid A H, Fanning T G, Hultin J V, Taubenberger J K (1999) "Origin and evolution of the 1918 'Spanish' influenza virus hemagglutinin gene." *Proc Natl Acad Sci USA* 96(4): 1651-1656.

22. Ronaghi M, Uhlen M, Nyren P (1998) "A sequencing method based on real-time pyrophosphate." *Science* 281 (5375): 363, 365.

23. Scheffner M (1998) "Ubiquitin, E6-AP, and their role in p53 inactivation." *Pharmacol Ther* 78(3): 129-139.

24. Schmidt N J, Emmons R W, American Public Health Association. Committee on Laboratory Standards and Practices. (1989) "Diagnostic procedures for viral, rickettsial, and chlamydial infections." Washington, D.C.: American Public Health Association. xv, 1225 p. p.

25. Shinya K, Hatta M, Yamada S, Takada A, Watanabe S et al., (2005) "Characterization of a human H5N1 influenza A virus isolated in 2003." *J Virol* 79(15): 9926-9932.

26. Stevens J, Blixt O, Tumpey T M, Taubenberger J K, Paulson J C et al., (2006a) "Structure and receptor specificity of the hemagglutinin from an H5N1 influenza virus." *Science* 312(5772): 404-410.

27. Stevens J, Blixt O, Glaser L, Taubenberger J K, Palese P et al., (2006b) "Glycan microarray analysis of the hemagglutinins from modern and pandemic influenza viruses reveals different receptor specificities." *J Mol Biol* 355(5): 1143-1155.

28. Subbarao K, Klimov A, Katz J, Regnery H, Lim W et al., (1998) Characterization of an avian influenza A (H5N1) virus isolated from a child with a fatal respiratory illness. *Science* 279(5349): 393-396.

29. Templeton K E, Schelting a S A, Beersma M F, Kroes A C, Claas E C (2004) Rapid and sensitive method using multiplex real-time PCR for diagnosis of infections by influenza a and influenza B viruses, respiratory syncytial virus, and parainfluenza viruses 1, 2, 3, and 4. *J Clin Microbiol* 42(4): 1564-1569.

30. Thompson J D, Gibson T J, Plewniak F, Jeanmougin F, Higgins D G (1997) The CLUSTAL_X windows interface: flexible strategies for multiple sequence alignment aided by quality analysis tools. *Nucleic Acids Res* 25(24): 4876-4882.

31. Vines A, Wells K, Matrosovich M, Castrucci M R, Ito T et al., (1998) The role of influenza A virus hemagglutinin residues 226 and 228 in receptor specificity and host range restriction. *J Virol* 72(9): 7626-7631.

32. Whiley D M, Sloots T P (2005) A 5'-nuclease real-time reverse transcriptase-polymerase chain reaction assay for the detection of a broad range of influenza A subtypes, including H5N1. *Diagn Microbiol Infect Dis.*

33. WHO (2005) World Health Organization Global Influenza Program Surveillance Network, "Evolution of H5N1 avian influenza viruses in Asia," *Emerg Infect Dis* 11, 2005. (http(dot)//www(dot)cdc(dot)gov/ncidod/eid/vol11no10/pdfs/05-0644(dot)pdf).

34. Xu X, Subbarao, Cox N J, Guo Y (1999) "Genetic characterization of the pathogenic influenza A/Goose/Guangdong/1/96 (H5N1) virus: similarity of its hemagglutinin gene to those of H5N1 viruses from the 1997 outbreaks in Hong Kong." *Virology* 261(1): 15-19.

What is claimed is:

1. A method for detecting the presence of an influenza A virus and identifying its strain by determining selected subsequences of its hemagglutinin (HA) gene, comprising:

(a) obtaining a sample possibly containing an influenza A virus;

(b) obtaining DNA having a sequence from an HA gene in a virus in the sample;

(c) obtaining sequence information for at least three portions of the DNA from step (b), wherein said three portions are (i) a glycosylation sequon; (ii) a receptor-binding site; and (iii) an HA1/HA2 cleavage site, whereby said sequence information from said three portions together detects the strain of the influenza A virus.

2. The method of claim 1 wherein said sequence information is obtained by sequencing less than 30 bases for each of said (i) a glycosylation sequon; (ii) receptor-binding site; and (iii) HA1/HA2 cleavage site.

3. The method of claim 2 wherein the sequencing is done using pyrosequencing.

4. The method of claim 1 wherein obtaining sequence information further comprises a step of detecting hybridization of sample to a probe which hybridizes to a sequence of (i) a glycosylation sequon; (ii) a receptor-binding site; or (iii) an HA1/HA2 cleavage site.

5. The method of claim 1 wherein the DNA of step (b) is immobilized on a surface selected from a bead or a well.

6. The method of claim 1 wherein said DNA is obtained by RT-PCR.

7. The method of claim 6 wherein the RT-PCR is done with primers, which will amplify all of SEQ ID NOs 3 through 21.

8. The method of claim 1 further comprising obtaining sequence information of strain markers 1, 2 and 3, wherein strain marker 1 has a sequence selected from the group consisting of SEQ ID NO: 32, SEQ ID NO: 33, SEQ ID NO: 34, SEQ ID NO: 35, SEQ ID NO: 36, SEQ ID NO: 37, SEQ ID NO: 38 and SEQ ID NO: 39; strain marker 2 has a sequence selected from the group consisting of SEQ ID NO: 47, SEQ ID NO: 48, and SEQ ID NO: 49; and strain marker 3 has a sequence selected from the group consisting of SEQ ID NO: 73, SEQ ID NO: 74, SEQ ID NO: 75, and SEQ ID NO: 76.

9. The method of claim 8 further comprising sequencing one or more regions of the HA gene indicative of clade, as set forth in Clade Marker 1 and Clade Marker 2, wherein Clade Marker 1 has a sequence selected from the group consisting of SEQ ID NO: 25, SEQ ID NO: 26, SEQ ID NO: 27, SEQ ID NO: 28, SEQ ID NO: 29, SEQ ID NO: 30, and SEQ ID NO: 31; and Clade Marker 2 has a sequence selected from the group consisting of SEQ ID NO: 50, SEQ ID NO: 51, SEQ ID NO: 52, SEQ ID NO: 53, SEQ ID NO: 54 SEQ ID NO: 55, SEQ ID NO: 56, SEQ ID NO: 57, SEQ ID NO: 58, SEQ ID NO: 59, SEQ ID NO: 60, SEQ ID NO: 61 SEQ ID NO: 62, and SEQ ID NO: 63.

10. The method of claim 9 further comprising sequencing an HA cleavage site as identified by a sequence selected from the group consisting of SEQ ID NO: 78, SEQ ID NO: 79, SEQ ID NO: 80, SEQ ID NO: 81, SEQ ID NO: 82, and SEQ ID NO: 83.

11. The method of claim 1 wherein nucleotides A, T, G, and C are added in a predetermined order based on an expected sequence of regions (i) a glycosylation sequon; (ii) a receptor-binding site; and (iii) an HA1/HA2 cleavage site.

12. A method for analyzing an H5N1 influenza strain comprising the steps of obtaining cDNA from a sample possibly containing an H5N1 influenza virus and further obtaining a cDNA sequence according to at least one marker and correlating the marker to a corresponding strain as follows:

(a) Goose/Guangdong/1/96, correlates to at least one sequence selected from the group consisting of SEQ ID NO: 25, SEQ ID NO: 32, SEQ ID NO: 40, SEQ ID NO: 47, and SEQ ID NO: 50;

(b) HongKong/156/97 correlates to at least one sequence selected from the group consisting of SEQ ID NO: 25, SEQ ID NO: 33, SEQ ID NO: 41, SEQ ID NO: 47, SEQ ID NO: 50;

(c) Hong Kong/483/97 correlates to at least one sequence selected from the group consisting of SEQ ID NO:25, SEQ ID NO:34, SEQ ID NO:41, SEQ ID NO:47, and SEQ ID NO: 51;

(d) HongKong/213/03 correlates to at least one sequence selected from the group consisting of SEQ ID NO:26, SEQ ID NO: 35, SEQ ID NO: 42 SEQ ID NO: 47, and SEQ ID NO:51;

(e) Chicken/Korea/ES/03 correlates to at least one sequence selected from the group consisting of SEQ ID NO: 27, SEQ ID NO: 36, SEQ ID NO: 43, SEQ ID NO: 48, and SEQ ID NO: 52, (f) Vietnam/1203/04 correlates to at least one sequence selected from the group consisting of SEQ ID NO: 28, SEQ ID NO: 37, SEQ ID NO: 41, SEQ ID NO: 47, and SEQ ID NO: 53, (g) Vietnam/JP14/05 correlates to at least one sequence selected from the group consisting of SEQ ID NO: 29, SEQ ID NO: 38, SEQ ID NO: 44, SEQ ID NO: 47, and SEQ ID NO: 54;

(h) Vietnam/HN304/08/05 correlates to at least one sequence selected from the group consisting of SEQ ID NO: 30, SEQ ID NO: 38, SEQ ID NO: 45, SEQ ID NO: 47, and SEQ ID NO: 55; and (i) Indonesia/5/05 correlates to at least one sequence selected from the group consisting of SEQ ID NO: 31, SEQ ID NO: 39, SEQ ID NO: 46, SEQ ID NO: 49 and SEQ ID NO: 53.

* * * * *